(12) United States Patent
Herrera-Estrella et al.

(10) Patent No.: US 12,098,376 B2
(45) Date of Patent: Sep. 24, 2024

(54) TRANSGENIC PLANTS AND FUNGI CAPABLE OF METABOLIZING PHOSPHITE AS A SOURCE OF PHOSPHORUS

(71) Applicant: Centro de Investigación y de Estudios Avanzados del Instituto Politécnico Nacional (CINVESTAV), Mexico City (MX)

(72) Inventors: Luis R. Herrera-Estrella, Irapuato (MX); Damar L. López-Arredondo, Irapuato (MX); Alfredo Heriberto Herrera-Estrella, Irapuato (MX)

(73) Assignee: Centro de Investigación y de Estudios Avanzados del Instituto Politécnico Nacional (CINVESTAV), Mexico City (MX)

( * ) Notice: Subject to any disclaimer, the term of this patent is extended or adjusted under 35 U.S.C. 154(b) by 676 days.

(21) Appl. No.: 17/107,802

(22) Filed: Nov. 30, 2020

(65) Prior Publication Data

US 2021/0324402 A1     Oct. 21, 2021

Related U.S. Application Data

(63) Continuation of application No. 13/560,618, filed on Jul. 27, 2012, now Pat. No. 10,851,386, which is a continuation of application No. 13/130,285, filed as application No. PCT/IB2009/007741 on Nov. 19, 2009, now abandoned.

(60) Provisional application No. 61/199,784, filed on Nov. 19, 2008.

(51) Int. Cl.
| | |
|---|---|
| C12N 15/82 | (2006.01) |
| C05D 9/00 | (2006.01) |
| C07K 14/21 | (2006.01) |
| C12N 9/00 | (2006.01) |
| C12N 9/02 | (2006.01) |

(52) U.S. Cl.
CPC ........... *C12N 15/8274* (2013.01); *C05D 9/00* (2013.01); *C07K 14/21* (2013.01); *C12N 9/0004* (2013.01); *C12N 15/8261* (2013.01); *C12N 15/8282* (2013.01)

(58) Field of Classification Search
None
See application file for complete search history.

(56) References Cited

U.S. PATENT DOCUMENTS

| | | | | |
|---|---|---|---|---|
| 5,514,200 | A * | 5/1996 | Lovatt | C05G 5/23 71/64.1 |
| 2004/0035162 | A1* | 2/2004 | Williams | C05D 9/00 71/28 |
| 2004/0091985 | A1* | 5/2004 | Metcalf | C12P 19/36 435/189 |
| 2008/0105018 | A1* | 5/2008 | Grech | C12P 3/00 71/7 |

* cited by examiner

*Primary Examiner* — Wayne A Langel
(74) *Attorney, Agent, or Firm* — Psi Star Intellectual Property LLC

(57) ABSTRACT

System, including methods and compositions, for making and using transgenic plants and/or transgenic fungi that metabolize phosphite as a source of phosphorus for supporting growth.

15 Claims, 7 Drawing Sheets

Specification includes a Sequence Listing.

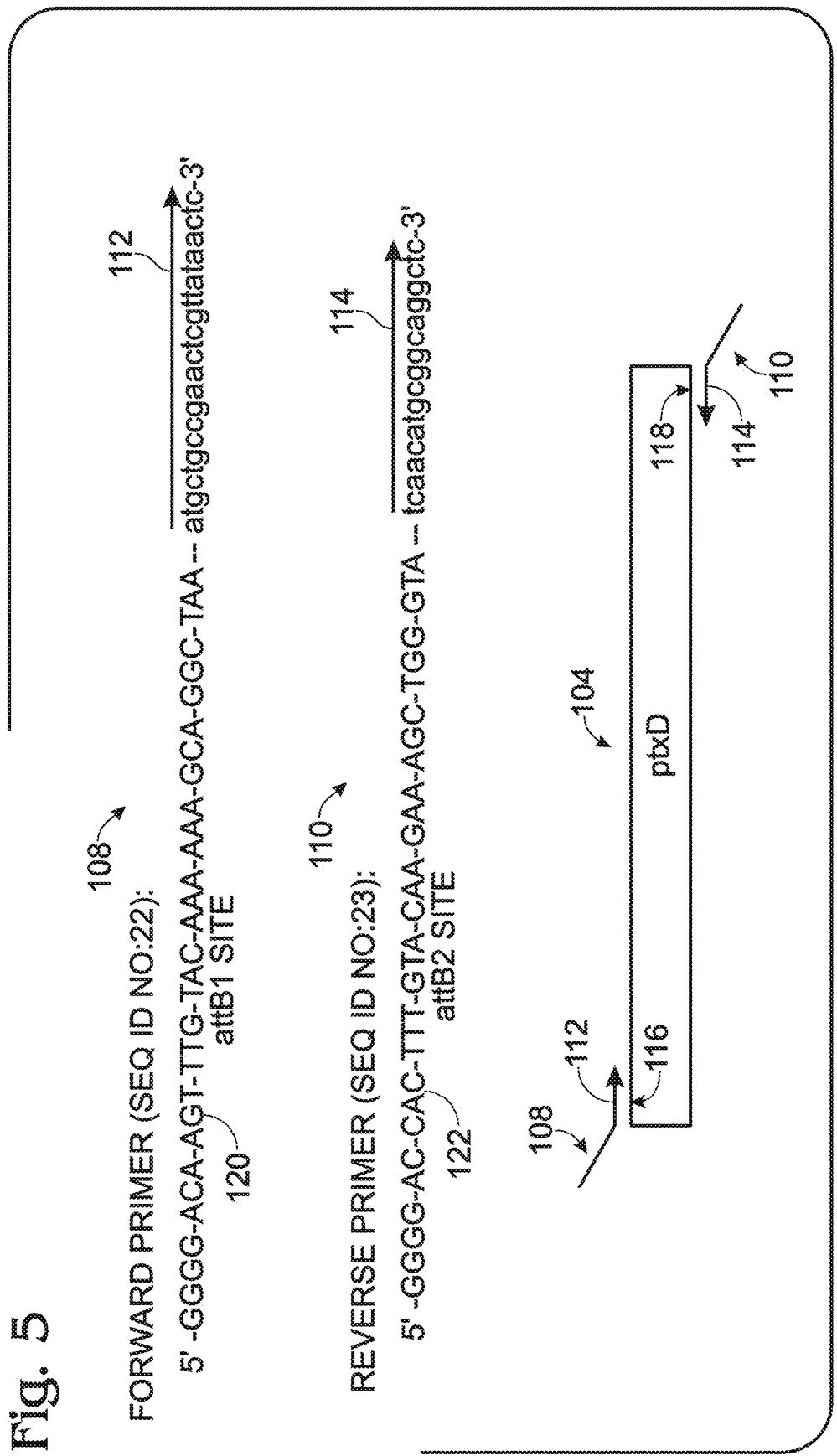

SEQUENCE LISTING

<160> NUMBER OF SEQ ID NOS: 23

<210> SEQ ID NO 1
<211> LENGTH: 336
<212> TYPE: PRT
<213> ORGANISM: Pseudomonas stutzeri

<400> SEQUENCE: 1

```
Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255
```

Gly Tyr Ala Ala Asp Val Phe Glu Met Glu Asp Trp Ala Arg Ala Asp
                260                 265                 270

Arg Pro Arg Leu Ile Asp Pro Ala Leu Leu Ala His Pro Asn Thr Leu
            275                 280                 285

Phe Thr Pro His Ile Gly Ser Ala Val Arg Ala Val Arg Leu Glu Ile
        290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 2
<211> LENGTH: 335
<212> TYPE: PRT
<213> ORGANISM: Acinetobacter radioresistens

<400> SEQUENCE: 2

Met Lys Gln Lys Ile Val Leu Thr His Trp Val His Pro Glu Ile Ile
1               5                   10                  15

Asp Tyr Leu Gln Ser Val Ala Asp Val Val Pro Asn Met Thr Arg Asp
                20                  25                  30

Thr Met Ser Arg Ala Glu Leu Leu Glu Arg Ala Lys Asp Ala Asp Ala
            35                  40                  45

Leu Met Val Phe Met Pro Asp Ser Ile Asp Asp Phe Leu Ala Ser
        50                  55                  60

Cys Pro Lys Leu Lys Ile Val Ser Ala Ala Leu Lys Gly Tyr Asp Asn
65                  70                  75                  80

Phe Asp Val Asp Ala Cys Thr Arg Arg Gly Ile Trp Phe Ser Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Leu Ala Glu Gly Asp Arg Arg Ile Arg Thr
        115                 120                 125

His Gly Phe Asn Gly Trp Arg Pro Glu Leu Tyr Gly Thr Gly Leu Thr
    130                 135                 140

Gly Arg Thr Leu Gly Ile Ile Gly Met Gly Ala Val Gly Arg Ala Ile
145                 150                 155                 160

Ala Lys Arg Leu Ser Ser Phe Asp Met Arg Val Leu Tyr Cys Asp Asp
                165                 170                 175

Ile Ala Leu Asn Gln Glu Gln Glu Lys Ala Trp Asn Ala Arg Gln Val
            180                 185                 190

Ser Leu Asp Glu Leu Leu Ser Ser Asp Phe Val Val Pro Met Leu
        195                 200                 205

Pro Met Thr Pro Gln Thr Leu His Leu Leu Asn Ala Glu Thr Ile Gly
    210                 215                 220

Thr Met Arg Thr Gly Ser Tyr Leu Ile Asn Ala Cys Arg Gly Ser Val
225                 230                 235                 240

Val Asp Glu Leu Ala Val Ala Glu Ala Leu Ser Gly Lys Leu Ala
                245                 250                 255

Gly Tyr Ala Ala Asp Val Phe Glu Leu Glu Glu Trp Ile Arg Val Asp
            260                 265                 270

Arg Pro Thr Ala Ile Pro Gln Glu Leu Leu Thr Asn Thr Ala Gln Thr
        275                 280                 285

```
Phe Phe Thr Pro His Leu Gly Ser Ala Val Asp Asp Val Arg Phe Glu
    290                 295                 300

Ile Glu Gln Leu Ala Ala Asn Asn Ile Leu Gln Ala Leu Thr Gly Gln
305                 310                 315                 320

Arg Pro Ser Asp Ala Ile Asn Asn Pro Ile Leu Glu Gly Val Asn
                325                 330                 335

<210> SEQ ID NO 3
<211> LENGTH: 333
<212> TYPE: PRT
<213> ORGANISM: Alcaligenes faecalis

<400> SEQUENCE: 3

Met Lys Pro Arg Ile Val Thr Thr His Arg Ile His Pro Asp Thr Leu
1               5                   10                  15

Ala Leu Leu Glu Thr Ala Ala Glu Val Ile Ser Asn Gln Ser Asp Ser
                20                  25                  30

Thr Met Ser Arg Glu Glu Val Leu Leu Arg Thr Asn Asp Ala Asp Gly
            35                  40                  45

Met Met Val Phe Met Pro Asp Ser Ile Asp Ala Asp Phe Leu Ser Ala
        50                  55                  60

Cys Pro Asn Leu Lys Val Ile Gly Ala Ala Leu Lys Gly Tyr Asp Asn
65                  70                  75                  80

Phe Asp Val Glu Ala Cys Thr Arg His Gly Ile Trp Phe Thr Ile Val
                85                  90                  95

Pro Asp Leu Leu Thr Ser Pro Thr Ala Glu Leu Thr Ile Gly Leu Leu
            100                 105                 110

Leu Ser Ile Thr Arg Asn Met Leu Gln Gly Asp Asn Tyr Ile Arg Ser
        115                 120                 125

Arg Gln Phe Asn Gly Trp Thr Pro Arg Phe Tyr Gly Thr Gly Leu Thr
    130                 135                 140

Gly Lys Thr Ala Gly Ile Ile Gly Thr Gly Ala Val Gly Arg Ala Val
145                 150                 155                 160

Ala Lys Arg Leu Ala Ala Phe Asp Met Gln Ile Gln Tyr Thr Asp Pro
                165                 170                 175

Gln Pro Leu Pro Gln Glu Ser Glu Arg Ala Trp Asn Ala Ser Arg Thr
            180                 185                 190

Ser Leu Asp Gln Leu Leu Ala Thr Ser Asp Phe Ile Ile Pro Met Leu
        195                 200                 205

Pro Met Ser Ser Asp Thr His His Thr Ile Asn Ala Arg Ala Leu Asp
    210                 215                 220

Arg Met Lys Pro Gly Ala Tyr Leu Val Asn Ala Cys Arg Gly Ser Ile
225                 230                 235                 240

Val Asp Glu Arg Ala Val Val His Ala Leu Arg Thr Gly His Leu Gly
                245                 250                 255

Gly Tyr Ala Ala Asp Val Phe Glu Met Glu Glu Trp Ala Arg Pro Asp
            260                 265                 270

Arg Pro His Ser Ile Pro Asp Glu Leu Leu Asp Pro Ala Leu Pro Thr
        275                 280                 285

Phe Phe Thr Pro His Leu Gly Ser Ala Val Lys Ser Val Arg Met Glu
    290                 295                 300

Ile Glu Arg Glu Ala Ala Leu Ser Ile Leu Glu Ala Leu Gln Gly Arg
305                 310                 315                 320
```

```
Ile Pro Arg Gly Ala Val Asn His Val Gly Ala Gly Arg
                325                 330

<210> SEQ ID NO 4
<211> LENGTH: 332
<212> TYPE: PRT
<213> ORGANISM: Cyanothece sp. CCY0110

<400> SEQUENCE: 4

Met Ser Gln Lys Pro Lys Val Val Ile Thr His Trp Ile His Pro Glu
1               5                   10                  15

Val Ile Asp Tyr Leu Asn Pro Tyr Cys Glu Leu Ile Leu Asn Gln Thr
            20                  25                  30

Lys Glu Thr Leu Ser Arg Glu Glu Val Ile Asn Arg Ser Arg Asn Ala
        35                  40                  45

Gln Gly Leu Met Val Phe Met Pro Asp His Ile Asp Val Lys Phe Leu
    50                  55                  60

Glu Ala Cys Pro Asn Leu Lys Val Ile Ser Gly Ala Leu Arg Gly Tyr
65                  70                  75                  80

Asp Asn Phe Asp Val Glu Ala Cys Thr Lys His Asn Ile Trp Phe Thr
                85                  90                  95

Ile Val Pro Asp Leu Leu Ala Ala Pro Thr Ala Glu Leu Thr Ile Gly
            100                 105                 110

Leu Leu Ile Ile Leu Ala Arg Arg Met Leu Glu Gly Asp Arg Leu Ile
        115                 120                 125

Arg Ser Asp Asn Phe Gln Gly Trp Lys Pro Gln Leu Tyr Gly Thr Gly
    130                 135                 140

Leu Leu Asn Lys Ser Leu Gly Ile Ile Gly Met Gly Lys Leu Gly Lys
145                 150                 155                 160

Ala Leu Ala Lys Arg Leu Val Gly Phe Asp Met Asn Leu Leu Tyr Thr
                165                 170                 175

Asp Pro Ile Ser Leu Thr Asn Gln Gln Glu Lys Asp Trp Lys Ile Ser
            180                 185                 190

Lys Thr Ser Leu Glu Glu Leu Leu Ser Lys Ser Asp Tyr Val Val Leu
        195                 200                 205

Met Val Ser Leu Val Pro Asp Thr Tyr His Leu Ile Asn Glu Asn Thr
    210                 215                 220

Leu Lys Leu Met Lys Pro Lys Ser Phe Leu Ile Asn Pro Cys Arg Gly
225                 230                 235                 240

Ser Val Val Asp Glu Asn Ala Ile Ala Asp Ala Ile Lys Ser Gly His
                245                 250                 255

Leu Ala Gly Tyr Ala Ala Asp Val Phe Glu Met Glu Asp Trp Ala Ile
            260                 265                 270

Ala Asn Arg Pro Lys Ser Ile Asn Gln Thr Leu Leu Thr Asp Ile Lys
        275                 280                 285

His Thr Phe Phe Thr Pro His Leu Gly Ser Ala Ile Asn Asp Val Arg
    290                 295                 300

Arg Glu Ile Ala Ile Glu Ala Ala Lys Asn Ile Ile Glu Val Phe Ser
305                 310                 315                 320

Asp Asn Arg Pro Lys Ser Ala Ile Asn Asn Ile Ile
                325                 330

<210> SEQ ID NO 5
<211> LENGTH: 335
<212> TYPE: PRT
```

<213> ORGANISM: Gallionella ferruginea

<400> SEQUENCE: 5

Met Lys Pro Lys Ile Val Ile Thr Ser Trp Val His Pro Gln Thr Leu
1               5                   10                  15

Asp Met Leu Arg Pro His Cys Asp Val Val Ala Asn Glu Thr Arg Glu
            20                  25                  30

Arg Leu Ser Arg Glu Glu Ile Ile Lys Arg Cys Ser Asp Ala Val Ala
        35                  40                  45

Val Met Thr Phe Met Pro Asp Ser Ile Asp Asp Ala Phe Leu Ala Glu
    50                  55                  60

Cys Pro Gln Leu Arg Leu Val Ala Cys Ala Leu Lys Gly Tyr Asp Asn
65                  70                  75                  80

Tyr Asp Val Ala Ala Cys Thr Arg Arg Gly Val Arg Ile Thr Asn Val
                85                  90                  95

Pro Asp Leu Leu Thr Ile Pro Thr Ala Glu Leu Thr Val Gly Leu Leu
            100                 105                 110

Ile Gly Leu Thr Arg Lys Val Leu Gln Gly Asp Arg Phe Val Arg Ser
        115                 120                 125

Gly Gln Phe Thr Gly Trp Arg Pro Met Leu Tyr Gly Ala Gly Leu Thr
    130                 135                 140

Gly Arg Thr Leu Gly Ile Ile Gly Met Gly Ala Val Gly Arg Ala Ile
145                 150                 155                 160

Ala Ala Arg Leu Gln Gly Tyr Glu Met Glu Leu Leu Tyr Thr Asp Pro
                165                 170                 175

Gln Pro Leu Pro Pro Glu Leu Glu Ala Arg Leu Gly Leu Arg Lys Val
            180                 185                 190

Gly Leu Val Gln Leu Leu Ala Glu Ser Asp Tyr Val Val Pro Met Val
        195                 200                 205

Pro Tyr Thr Gln Asp Thr Leu His Met Ile Asn Ala Ala Ser Leu Ser
    210                 215                 220

Ile Met Lys Pro Gly Ala Tyr Leu Val Asn Thr Cys Arg Gly Ser Val
225                 230                 235                 240

Val Asp Glu Lys Ala Val Ala Asp Ala Leu Asp Ser Gly Lys Leu Ala
                245                 250                 255

Gly Tyr Ala Ala Asp Val Phe Glu Leu Glu Glu Trp Met Arg Pro Asp
            260                 265                 270

Arg Pro Glu Ser Ile Ser Glu Arg Leu Leu Ser Asn Thr Glu Leu Thr
        275                 280                 285

Leu Phe Thr Pro His Ile Gly Ser Ala Val Asp Thr Val Arg Leu Ala
    290                 295                 300

Ile Glu Met Glu Ala Ala Thr Asn Ile Leu Gln Val Leu Lys Gly Gln
305                 310                 315                 320

Ile Pro Gln Gly Ala Ile Asn His Pro Leu Asp Lys Val Ala Val
                325                 330                 335

<210> SEQ ID NO 6
<211> LENGTH: 336
<212> TYPE: PRT
<213> ORGANISM: Janthinobacterium sp. Marseille

<400> SEQUENCE: 6

Met Lys Pro Lys Ile Val Ile Thr His Trp Val His Pro Glu Ile Val
1               5                   10                  15

Glu Met Leu Ser Ser Val Ala Glu Val Val Thr Asn Asp Thr Leu Glu
            20                  25                  30

Thr Leu Pro Arg Glu Glu Leu Leu Arg Arg Ser Lys Asp Ala Asp Ala
            35                  40                  45

Val Met Ala Phe Met Pro Asp Ser Val Asp Ser Phe Leu Ala Ala
50                  55                  60

Cys Pro Lys Leu Lys Ile Val Phe Ala Ala Leu Lys Gly Tyr Asp Asn
65                  70                  75                  80

Phe Asp Val Asp Ala Cys Thr Lys Arg Gly Val Trp Phe Gly Ile Val
                85                  90                  95

Pro Asp Leu Leu Thr Val Pro Thr Ala Glu Leu Thr Val Gly Leu Leu
            100                 105                 110

Leu Gly Leu Thr Arg His Val Met Ala Gly Asp Asp His Val Arg Ser
            115                 120                 125

Gly Thr Phe His Gly Trp Arg Pro Lys Leu Tyr Gly Ala Gly Leu Ala
130                 135                 140

Gly Ser Thr Ile Gly Ile Ile Gly Met Gly Arg Val Gly Lys Ala Ile
145                 150                 155                 160

Ala Lys Arg Leu Ser Gly Phe Glu Met Asn Ala Val Tyr Cys Asp Ser
                165                 170                 175

Val Pro Leu Asn Pro Val Asp Glu Gln Ala Trp Asn Ala Arg Gln Val
            180                 185                 190

Ser Phe Asp Glu Leu Leu Thr Cys Ser Asp Phe Val Val Pro Met Leu
            195                 200                 205

Pro Met Thr Ser Asp Thr Phe His Leu Ile Asp Ala His Ala Ile Ser
210                 215                 220

Lys Met Arg Arg Gly Ser Tyr Leu Leu Asn Thr Ser Arg Gly Ser Val
225                 230                 235                 240

Val Asp Glu Asn Ala Val Val Glu Ala Leu Asn Gln Gly His Leu Ala
                245                 250                 255

Gly Tyr Ala Ala Asp Val Phe Glu Met Glu Glu Trp Ala Arg Pro Asp
            260                 265                 270

Arg Pro Leu Thr Val Pro Gln Ala Leu Leu Asn Asn Arg Thr Gln Thr
            275                 280                 285

Leu Phe Thr Pro His Val Gly Ser Gly Val Lys Lys Val Arg Leu Glu
290                 295                 300

Ile Glu Arg Tyr Ser Ala His Ser Ile Leu Gln Ala Leu Ala Gly Gln
305                 310                 315                 320

Arg Pro Asp Gly Ala Leu Asn Glu Pro Leu Lys Ala Ser Val Ala Ala
                325                 330                 335

<210> SEQ ID NO 7
<211> LENGTH: 336
<212> TYPE: PRT
<213> ORGANISM: Klebsiella pneumoniae

<400> SEQUENCE: 7

Met Leu Pro Lys Leu Val Ile Thr His Arg Val His Asp Glu Ile Leu
1               5                   10                  15

Gln Leu Leu Ala Pro His Cys Glu Leu Val Thr Asn Gln Thr Asp Ser
            20                  25                  30

Thr Leu Thr Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
            50                  55                  60

Cys Pro Glu Leu Arg Val Val Gly Cys Ala Leu Lys Gly Phe Asp Asn
 65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
                100                 105                 110

Val Gly Leu Gly Arg His Leu Arg Ala Ala Asp Ala Phe Val Arg Ser
            115                 120                 125

Gly Glu Phe Gln Gly Trp Gln Pro Gln Phe Tyr Gly Thr Gly Leu Asp
130                 135                 140

Asn Ala Thr Val Gly Ile Leu Gly Met Gly Ala Ile Gly Leu Ala Met
145                 150                 155                 160

Ala Glu Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 8
<211> LENGTH: 336
<212> TYPE: PRT
<213> ORGANISM: Marinobacter algicola

<400> SEQUENCE: 8

Met Lys Pro Arg Val Val Ile Thr His Arg Val His Asp Ser Ile Leu
1               5                   10                  15

Ala Ser Leu Glu Pro His Cys Glu Leu Ile Thr Asn Gln Ser Ala Val
            20                  25                  30

Thr Leu Pro Pro Asp Ser Val Arg Ala Arg Ala Thr Ala Asp Ala
        35                  40                  45

Met Met Ala Phe Met Pro Asp Arg Val Ser Glu Glu Phe Leu Val Ala
            50                  55                  60

Cys Pro Asp Leu Lys Val Ile Gly Ala Ala Leu Lys Gly Phe Asp Asn
 65                  70                  75                  80

Phe Asp Val Asp Ala Cys Thr Arg His Gly Val Trp Leu Thr Phe Val
            85                  90                  95

Pro Asp Leu Leu Thr Val Pro Thr Ala Glu Leu Thr Val Gly Leu Thr
            100                 105                 110

Ile Gly Leu Ile Arg Gln Ile Arg Pro Ala Asp Gln Phe Val Arg Ser
            115                 120                 125

Gly Glu Phe Gln Gly Trp Gln Pro Gln Phe Tyr Gly Leu Gly Ile Glu
            130                 135                 140

Gly Ser Thr Ile Gly Ile Val Gly Met Gly Ala Ile Gly Lys Ala Val
145                 150                 155                 160

Ala Thr Arg Leu Gln Gly Trp Gly Ala Arg Val Leu Tyr Ser Gln Pro
                165                 170                 175

Glu Ser Leu Pro Ala Ala Glu Glu Gly Ala Leu Gly Leu Ser Arg Ser
            180                 185                 190

Glu Leu Asp Asp Leu Leu Ala Glu Ser Asp Ile Val Ile Leu Ala Leu
            195                 200                 205

Ala Leu Asn Glu His Thr Leu His Thr Leu Asn Ala Asp Arg Leu Arg
            210                 215                 220

Gln Met Lys Arg Gly Ser Phe Leu Ile Asn Pro Cys Arg Gly Ser Val
225                 230                 235                 240

Val Asp Glu Ala Ala Val Leu Gln Ser Leu Thr Tyr Gly His Leu Ser
                245                 250                 255

Gly Tyr Ala Ala Asp Val Phe Glu Met Glu Asp Trp Ala Arg Pro Asp
            260                 265                 270

Arg Pro Gln Arg Ile Asp Pro Ala Leu Leu Ala His Pro Asn Thr Leu
            275                 280                 285

Phe Thr Ala His Thr Gly Ser Ala Val Arg Asp Val Arg Phe Ala Ile
            290                 295                 300

Glu Leu Arg Ala Ala Asp Asn Ile Leu Gln Ala Leu Arg Gly His Gln
305                 310                 315                 320

Pro Gln Asp Ala Val Asn Ser Pro Leu Glu Pro Lys Gly Thr Val Cys
                325                 330                 335

<210> SEQ ID NO 9
<211> LENGTH: 339
<212> TYPE: PRT
<213> ORGANISM: Methylobacterium extorquens

<400> SEQUENCE: 9

Met Arg Phe Lys Val Val Thr Asn Pro Val Phe Pro Glu Thr Arg
1               5                   10                  15

Glu Ile Leu Glu Gly Leu Cys Asp Val Asp Ile Asn Pro Gly Pro Glu
            20                  25                  30

Pro Trp Pro Ala Ala Glu Val Arg Ala Arg Cys Ser Asp Ala Asp Ala
            35                  40                  45

Leu Leu Ala Phe Met Thr Asp Cys Val Asp Ala Gly Phe Leu Glu Ala
            50                  55                  60

Cys Pro Arg Leu Lys Val Val Ala Cys Ala Leu Lys Gly Trp Asp Asn
65                  70                  75                  80

Phe Asp Val Glu Ala Cys Thr Arg Ser Gly Ile Trp Leu Thr Ala Val
            85                  90                  95

Pro Asp Leu Leu Thr Glu Pro Thr Ala Glu Leu Ala Val Gly Leu Ala
            100                 105                 110

Ile Gly Leu Cys Arg Asn Val Ala Gly Asp Arg Ala Val Arg Ala
            115                 120                 125

Gly Phe Asp Gly Trp Arg Pro Arg Leu Tyr Gly Ser Gly Leu Tyr Gly
130                 135                 140

Ser Val Gly Val Ala Gly Met Gly Lys Val Gly Arg Ala Ile Thr
145                 150                 155                 160

Arg Arg Leu Lys Gly Phe Gly Ala Arg Glu Leu Leu Tyr Phe Asp Glu
            165                 170                 175

Gln Ala Leu Pro Ala Ser Ala Glu Ala Glu Leu Gly Ala Cys Arg Val
            180                 185                 190

Ser Trp Asp Thr Leu Val Gly Arg Ser Asp Val Leu Ile Leu Ala Leu
            195                 200                 205

Pro Leu Thr Pro Asp Thr Arg His Met Leu Asp Ala Ala Ala Leu Ala
210                 215                 220

Ala Ala Ser Pro Gly Leu Arg Ile Val Asn Ala Gly Arg Gly Ser Val
225                 230                 235                 240

Val Asp Glu Ala Ala Val Ala Glu Ala Leu Ala Glu Gly Arg Leu Gly
            245                 250                 255

Gly Tyr Ala Ala Asp Val Phe Glu Met Glu Asp Trp Ala Leu Asp Asp
            260                 265                 270

Arg Pro Arg Arg Ile Ala Pro Gly Leu Leu Thr Val Glu Asp Arg Thr
            275                 280                 285

Leu Phe Thr Pro His Leu Gly Ser Gly Val Val Asp Thr Arg Arg Arg
290                 295                 300

Ile Glu Ala Ala Ala Ala His Asn Leu Leu Asp Ala Leu Lys Gly Leu
305                 310                 315                 320

Val Pro Ala Asp Ser Ile Asn His Pro Glu Ser Leu Arg Gly Phe Asp
            325                 330                 335

Gly Ala Asn

<210> SEQ ID NO 10
<211> LENGTH: 332
<212> TYPE: PRT
<213> ORGANISM: Nostoc sp. PCC 7120

<400> SEQUENCE: 10

Met Lys Pro Lys Val Val Ile Thr Asn Trp Val His Pro Glu Val Ile
1               5                   10                  15

Glu Leu Leu Lys Pro Ser Cys Glu Val Ile Ala Asn Pro Ser Lys Glu
            20                  25                  30

Ala Leu Ser Arg Glu Glu Ile Leu Gln Arg Ala Lys Asp Ala Glu Ala
            35                  40                  45

Leu Met Val Phe Met Pro Asp Thr Ile Asp Glu Ala Phe Leu Arg Glu
        50                  55                  60

Cys Pro Lys Leu Lys Ile Ile Ala Ala Ala Leu Lys Gly Tyr Asp Asn
65                  70                  75                  80

Phe Asp Val Ala Ala Cys Thr His Arg Gly Ile Trp Phe Thr Ile Val
                85                  90                  95

Pro Ser Leu Leu Ser Ala Pro Thr Ala Glu Ile Thr Ile Gly Leu Leu
            100                 105                 110

Ile Gly Leu Gly Arg Gln Met Leu Glu Gly Asp Arg Phe Ile Arg Thr
            115                 120                 125

Gly Lys Phe Thr Gly Trp Arg Pro Gln Phe Tyr Ser Leu Gly Leu Ala
        130                 135                 140

```
Asn Arg Thr Leu Gly Ile Val Gly Met Gly Ala Leu Gly Lys Ala Ile
145                 150                 155                 160

Ala Gly Arg Leu Ala Gly Phe Glu Met Gln Leu Leu Tyr Ser Asp Pro
                165                 170                 175

Val Ala Leu Pro Pro Glu Gln Glu Ala Thr Gly Asn Ile Ser Arg Val
            180                 185                 190

Pro Phe Glu Thr Leu Ile Glu Ser Ser Asp Phe Val Val Leu Val Val
        195                 200                 205

Pro Leu Gln Pro Ala Thr Leu His Leu Ile Asn Ala Asn Thr Leu Ala
    210                 215                 220

Lys Met Lys Pro Gly Ser Phe Leu Ile Asn Pro Cys Arg Gly Ser Val
225                 230                 235                 240

Val Asp Glu Gln Ala Val Cys Lys Ala Leu Glu Ser Gly His Leu Ala
                245                 250                 255

Gly Tyr Ala Ala Asp Val Phe Glu Met Glu Asp Trp Tyr Arg Ser Asp
            260                 265                 270

Arg Pro His Asn Ile Pro Gln Pro Leu Leu Glu Asn Thr Lys Gln Thr
        275                 280                 285

Phe Phe Thr Pro His Ile Gly Ser Ala Val Asp Glu Leu Arg His Asn
    290                 295                 300

Ile Ala Leu Glu Ala Ala Gln Asn Ile Leu Gln Ala Leu Gln Gly Gln
305                 310                 315                 320

Lys Pro Gln Gly Ala Val Asn Tyr Leu Arg Glu Ser
                325                 330

<210> SEQ ID NO 11
<211> LENGTH: 331
<212> TYPE: PRT
<213> ORGANISM: Oxalobacter formigenes

<400> SEQUENCE: 11

Met Asn Lys Gln Lys Val Val Leu Thr His Trp Val His Pro Glu Ile
1               5                   10                  15

Val Glu Met Leu Gln Glu Lys Thr Asp Val Val Ala Asn Leu Ser Arg
            20                  25                  30

Lys Thr Phe Thr Arg Asp Glu Leu Leu Glu Arg Ala Ala Ala Ala Asp
        35                  40                  45

Ala Leu Met Ala Phe Met Pro Asp Cys Ile Asp Glu Asp Phe Leu Lys
    50                  55                  60

Ala Cys Pro Lys Leu Lys Val Ile Gly Ala Ala Leu Lys Gly Tyr Asp
65                  70                  75                  80

Asn Phe Asp Val Lys Ala Cys Thr Glu Arg Gly Val Trp Leu Thr Ile
                85                  90                  95

Ala Pro Asp Leu Leu Thr Ile Pro Thr Ala Glu Leu Thr Val Gly Leu
            100                 105                 110

Val Leu Ala Ile Thr Arg Asn Met Leu Glu Gly Asp Arg His Ile Arg
        115                 120                 125

Ser Gly Gln Phe Asn Gly Trp Arg Pro Glu Leu Tyr Gly Leu Gly Leu
    130                 135                 140

His Lys Arg Thr Ala Gly Ile Ile Gly Met Gly Phe Val Gly Lys Ala
145                 150                 155                 160

Val Ala Glu Arg Leu Lys Gly Phe Gly Met Asp Ile Leu Tyr Ala Asp
                165                 170                 175
```

-continued

```
Gln Ser Pro Leu Ser Gln Glu Glu Arg Glu Leu Gly Leu Thr Arg
            180                 185                 190

Thr Gly Leu Pro Gln Leu Met His Ser Ser Asp Val Ile Pro Leu
            195                 200                 205

Leu Pro Leu Thr Glu Gln Thr Phe His Leu Phe Asp Lys Asp Ile Leu
210                 215                 220

Gly Gln Met Lys Gln Gly Ser Tyr Leu Val Asn Ala Cys Arg Gly Ser
225                 230                 235                 240

Val Val Asp Glu Lys Ala Val Val His Ser Leu Lys Thr Gly Gln Leu
            245                 250                 255

Ala Gly Tyr Ala Ala Asp Val Phe Glu Met Glu Asp Trp Ile Arg Ser
            260                 265                 270

Asp Arg Pro Arg Glu Ile Pro Gln Glu Leu Leu Asp Asn Thr Ala Gln
            275                 280                 285

Thr Phe Phe Thr Pro His Leu Gly Ser Ala Val Asp Glu Ile Arg Ile
            290                 295                 300

Glu Ile Glu Arg Tyr Cys Ala Thr Ser Ile Leu Gln Ala Leu Ala Gly
305                 310                 315                 320

Asp Ile Pro Asp Gly Arg Val Asn Asp Ile Arg
            325                 330

<210> SEQ ID NO 12
<211> LENGTH: 328
<212> TYPE: PRT
<213> ORGANISM: Streptomyces sviceus

<400> SEQUENCE: 12

Met Val Thr His Trp Ile His Pro Glu Val Asp Tyr Leu Arg Arg
1               5                   10                  15

Phe Cys Asp Pro Val Val Pro Val Glu Thr Glu Val Leu Gly Arg Arg
            20                  25                  30

Gln Cys Leu Glu Leu Ala Ala Asp Ala Asp Ala Leu Ile Met Cys Met
            35                  40                  45

Ala Asp Arg Val Asp Asp Phe Leu Ala Gln Cys Pro Arg Leu Arg
50                  55                  60

Val Ile Ser Thr Val Val Lys Gly Tyr Asp Asn Phe Asp Ala Glu Ala
65                  70                  75                  80

Cys Ala Arg Arg Gly Val Trp Leu Thr Val Leu Pro Asp Leu Leu Thr
            85                  90                  95

Ala Pro Thr Ala Glu Leu Ala Val Thr Leu Ala Val Ala Leu Gly Arg
            100                 105                 110

Arg Ile Arg Glu Gly Asp Ala Leu Met Arg Ser Gly Arg Tyr Asp Gly
            115                 120                 125

Trp Arg Pro Val Leu Tyr Gly Thr Gly Leu Tyr Arg Ser Arg Val Gly
            130                 135                 140

Val Val Gly Met Gly Arg Leu Gly Arg Ala Val Ala Arg Arg Leu Ser
145                 150                 155                 160

Gly Phe Glu Pro Ser Glu Val Leu Tyr Tyr Asp Lys Gln Pro Leu Gly
            165                 170                 175

Ala Ser Glu Glu Arg Arg Leu Gly Val Arg Ala Ala Gly Leu Glu Glu
            180                 185                 190

Leu Met Gly Arg Cys Gln Val Val Leu Ser Leu Leu Pro Leu Ala Met
            195                 200                 205
```

-continued

Asp Thr Arg His Leu Ile Gly Ser Asp Ala Ile Ala Ala Arg Pro
        210                 215                 220

Gly Gln Leu Leu Val Asn Val Gly Arg Gly Ser Val Val Asp Glu Asp
225                 230                 235                 240

Ala Val Ala Ala Ala Leu Asp Cys Gly Pro Leu Gly Gly Tyr Ala Ala
                245                 250                 255

Asp Val Phe Gly Cys Glu Asp Leu Thr Ala Pro Gly His Leu Arg Glu
                260                 265                 270

Val Pro Arg Arg Leu Leu Thr His Pro Arg Thr Leu Leu Thr Pro His
        275                 280                 285

Leu Gly Ser Ala Val Asp Val Ile Arg Arg Asp Met Glu Ile Ala Ala
        290                 295                 300

Ala His Gln Val Glu Gln Ala Leu Ser Gly Arg Val Pro Asp His Glu
305                 310                 315                 320

Val Thr Ala Gly Leu Leu Arg Glu
                325

<210> SEQ ID NO 13
<211> LENGTH: 336
<212> TYPE: PRT
<213> ORGANISM: Thioalkalivibrio sp. HL-EbGR7

<400> SEQUENCE: 13

Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
                20                  25                  30

Thr Leu Pro Arg Glu Glu Ile Leu Arg Arg Cys Arg Asp Ala Gln Ala
            35                  40                  45

Met Met Ala Phe Met Pro Asp Arg Val Asp Ala Asp Phe Leu Gln Ala
        50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Arg Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
            245                 250                 255

Gly Tyr Ala Ala Asp Val Phe Glu Met Glu Asp Trp Ala Arg Ala Asp
        260                 265                 270

Arg Pro Arg Leu Ile Asp Pro Ala Leu Leu Thr His Pro Asn Thr Leu
    275                 280                 285

Phe Thr Pro His Ile Gly Ser Ala Val Arg Ala Val Arg Leu Glu Ile
290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 14
<211> LENGTH: 331
<212> TYPE: PRT
<213> ORGANISM: Xanthobacter flavus

<400> SEQUENCE: 14

Met Ala Arg Lys Thr Ile Val Thr Asn Trp Val His Pro Glu Val Leu
1               5                   10                  15

Asp Leu Leu Ser Thr Arg Gly Pro Ala Glu Ala Asn Thr Thr Arg Glu
            20                  25                  30

Pro Trp Pro Arg Asp Glu Ile Ile Arg Arg Ala His Gly Ala Asp Ala
        35                  40                  45

Met Leu Ala Phe Met Thr Asp His Val Asp Ala Ala Phe Leu Asp Ala
    50                  55                  60

Cys Pro Glu Leu Lys Ile Val Ala Cys Ala Leu Lys Gly Ala Asp Asn
65                  70                  75                  80

Phe Asp Met Glu Ala Cys Arg Ala Arg Lys Val Ala Val Thr Ile Val
                85                  90                  95

Pro Asp Leu Leu Thr Ala Pro Thr Ala Glu Leu Ala Val Gly Leu Met
            100                 105                 110

Ile Thr Leu Gly Arg Asn Leu Leu Ala Gly Asp Arg Leu Ile Arg Glu
        115                 120                 125

Arg Pro Phe Ala Gly Trp Arg Pro Val Leu Tyr Gly Thr Gly Leu Asp
    130                 135                 140

Gly Ala Glu Val Gly Ile Val Gly Met Gly Ala Val Gly Gln Ala Ile
145                 150                 155                 160

Ala His Arg Leu Arg Pro Phe Arg Cys Arg Leu Ser Tyr Cys Asp Ala
                165                 170                 175

Arg Pro Leu Ser Pro Ala Ala Glu Asp Ala Gln Gly Leu Leu Arg Arg
            180                 185                 190

Asp Leu Ala Asp Leu Val Ala Arg Ser Asp Tyr Leu Val Leu Ala Leu
        195                 200                 205

Pro Leu Thr Pro Ala Ser Arg His Leu Ile Asp Ala Ala Ala Leu Ala
    210                 215                 220

Gly Met Lys Pro Gly Ala Leu Leu Ile Asn Pro Ala Arg Gly Ser Leu
225                 230                 235                 240

Val Asp Glu Ala Ala Val Ala Asp Ala Leu Glu Ala Gly His Leu Gly
                245                 250                 255

Gly Tyr Ala Ala Asp Val Phe Glu Thr Glu Asp Trp Ala Arg Pro Asp
            260                 265                 270

```
Arg Pro Ala Ala Ile Glu Ala Arg Leu Leu Ala His Pro Arg Thr Val
            275                 280                 285

Leu Thr Pro His Ile Gly Ser Ala Val Asp Ser Val Arg Arg Asp Ile
        290                 295                 300

Ala Leu Ala Ala Ala Arg Asp Ile Leu Arg His Leu Asp Gly Leu Gln
305                 310                 315                 320

Gln Asp Pro Pro Ser Arg Asp Arg Ser Ala Ala
                325                 330

<210> SEQ ID NO 15
<211> LENGTH: 10
<212> TYPE: PRT
<213> ORGANISM: Artificial Sequence
<220> FEATURE:
<223> OTHER INFORMATION: Consensus sequence for NAD-binding motif

<400> SEQUENCE: 15

Val Gly Ile Leu Gly Met Gly Ala Ile Gly
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Consensus signature sequence for the D-isomer
      specific 2-hydroxyacid family
<220> FEATURE:
<221> NAME/KEY: MISC_FEATURE
<222> LOCATION: (1)..(1)
<223> OTHER INFORMATION: Xaa presents Arg or Lys

<400> SEQUENCE: 16

Xaa Pro Gly Ala Leu Leu Val Asn Pro Cys Arg Gly Ser Val Val Asp
1               5                   10                  15

<210> SEQ ID NO 17
<211> LENGTH: 6
<212> TYPE: PRT
<213> ORGANISM: Artificial Sequence
<220> FEATURE:
<223> OTHER INFORMATION: Conserved signature sequence for the D-isomer
      specific 2-hydroxyacid family

<400> SEQUENCE: 17

Arg Gly Ser Val Val Asp
1               5

<210> SEQ ID NO 18
<211> LENGTH: 11
<212> TYPE: PRT
<213> ORGANISM: Artificial Sequence
<220> FEATURE:
<223> OTHER INFORMATION: Consensus motif that may enable hydrogenases to
      use phosphite as substrate

<400> SEQUENCE: 18

Gly Trp Gln Pro Gln Phe Tyr Gly Thr Gly Leu
1               5                   10

<210> SEQ ID NO 19
<211> LENGTH: 11
<212> TYPE: PRT
```

```
<213> ORGANISM: Artificial Sequence
<220> FEATURE:
<223> OTHER INFORMATION: Consensus motif that may enable hydrogenases to
      use phosphite as substrate
<220> FEATURE:
<221> NAME/KEY: MISC_FEATURE
<222> LOCATION: (3)..(3)
<223> OTHER INFORMATION: Xaa represents X1, which is Arg, Gln, Lys, or
      Thr
<220> FEATURE:
<221> NAME/KEY: MISC_FEATURE
<222> LOCATION: (5)..(5)
<223> OTHER INFORMATION: Xaa represents X2, which is Ala, Val, Gln, Arg,
      Lys, His, or Glu
<220> FEATURE:
<221> NAME/KEY: MISC_FEATURE
<222> LOCATION: (6)..(6)
<223> OTHER INFORMATION: Xaa represents X3, which is Leu or Phe
<220> FEATURE:
<221> NAME/KEY: MISC_FEATURE
<222> LOCATION: (8)..(8)
<223> OTHER INFORMATION: Xaa represents X4, which is Gly, Phe, or Ser
<220> FEATURE:
<221> NAME/KEY: MISC_FEATURE
<222> LOCATION: (9)..(9)
<223> OTHER INFORMATION: Xaa represents X5, which is Thr, Arg, Met, Leu,
      Ala, or Ser

<400> SEQUENCE: 19

Gly Trp Xaa Pro Xaa Xaa Tyr Xaa Xaa Gly Leu
1               5                   10

<210> SEQ ID NO 20
<211> LENGTH: 286
<212> TYPE: PRT
<213> ORGANISM: Pseudomonas stutzeri

<400> SEQUENCE: 20

Met Phe Ala Glu Gln Gln Arg Glu Tyr Leu Asp Lys Gly Tyr Thr Lys
1               5                   10                  15

Ile Glu Ser Phe Phe Ser Ala Glu Glu Val Ala Lys Ile Leu Glu Asp
                20                  25                  30

Val Lys Gln Ile Glu Leu Gly Ala Ile Gly Val Ala Ser Asp Asn Glu
            35                  40                  45

Thr Tyr Gln Phe Glu Lys Lys Asn Gly Glu Thr Thr Lys Leu Leu Arg
        50                  55                  60

Arg Val Glu Asn Pro His Leu Tyr Phe Asp Ala Ile Asp Ser Leu Val
65                  70                  75                  80

Arg Ser Glu Lys Ile Val Asp Leu Leu Arg His Phe Leu Gly Glu Asn
                85                  90                  95

Ile Arg Leu His Asn Ser Lys Ile Asn Phe Lys Pro Pro Ser Gly Ala
                100                 105                 110

Pro Val Gln Trp His Gln Asp Trp Ala Phe Tyr Pro His Thr Asn Asp
            115                 120                 125

Asp Phe Leu Thr Leu Gly Ile Phe Leu Asp Glu Thr Ser Glu Lys Asn
        130                 135                 140

Gly Ala Met Ala Cys Leu Pro Gly Ser His Lys Gly Lys Val Tyr Asp
145                 150                 155                 160

His Arg Asn Val Glu Thr Gly Glu Phe Cys His Ala Ile Ser Arg Ser
                165                 170                 175

Asn Trp Asp Glu Ala Leu Asp Pro Thr Glu Gly Glu Leu Leu Thr Gly
                180                 185                 190

Pro Val Gly Thr Val Thr Leu His His Val Arg Thr Leu His Gly Ser
            195                 200                 205
```

Gly Pro Asn His Ser Thr Ile Arg Arg Arg Phe Leu Leu Ile Gly Tyr
            210                 215                 220

Ala Ala Ala Asp Ala Trp Pro Leu Leu Gly Cys Gly Asn Tyr Gly Asp
225                 230                 235                 240

Tyr Glu Ser Leu Met Val Ser Gly Arg Ser Thr Val Phe Pro Arg Met
                245                 250                 255

Val Glu Leu Pro Leu Thr Val Pro Tyr Pro Leu Ser Met Tyr Gly Asp
            260                 265                 270

Arg Ile Phe Glu Ser Gln Arg Ala Leu Thr Gln Lys Tyr Tyr
            275                 280                 285

<210> SEQ ID NO 21
<211> LENGTH: 1011
<212> TYPE: DNA
<213> ORGANISM: Pseudomonas stutzeri

<400> SEQUENCE: 21
atgctgccga aactcgttat aactcaccga gtacacgatg agatcctgca actgctggcg      60
ccacattgcg agctgatgac caaccagacc gacagcacgc tgacgcgcga ggaaattctg    120
cgccgctgtc gcgatgctca ggcgatgatg gcgttcatgc cgatcgggt cgatgcagac     180 tttcttcaag cctgccctga gctgcgtgta gtcggctgcg cgctcaaggg cttcgacaat    240
ttcgatgtgg acgcctgtac tgcccgcggg gtctggctga ccttcgtgcc tgatctgttg    300
acggtcccga ctgccgagct ggcgatcgga ctggcggtgg ggctggggcg gcatctgcgg    360
gcagcagatg cgttcgtccg ctctggcgag ttccagggct ggcaaccaca gttctacggc    420
acggggctgg ataacgctac ggtcggcatc cttggcatgg cgccatcgg actggccatg     480 gctgatcgct tgcagggatg gggcgcgacc ctgcagtacc acgaggcgaa ggctctggat    540
acacaaaccg agcaacggct cggcctgcgc caggtggcgt gcagcgaact cttcgccagc    600
tcggacttca tcctgctggc gcttcccttg aatgccgata cccagcatct ggtcaacgcc    660
gagctgcttg ccctcgtacg gccgggcgct ctgcttgtaa accccgtgcg tggttcggta    720
gtggatgaag ccgccgtgct cgcggcgctt gagcgaggcc agctcggcgg gtatgcggcg    780
gatgtattcg aaatggaaga ctgggctcgc gcggaccggc gcggctgat cgatcctgcg     840 ctgctcgcgc atccgaatac gctgttcact ccgcacatag gtcggcagt gcgcgcggtg     900 cgcctggaga ttgaacgttg tgcagcgcag aacatcatcc aggtattggc aggtgcgcgc    960
ccaatcaacg ctgcgaaccg tctgcccaag gccgagcctg ccgcatgttg a            1011

<210> SEQ ID NO 22
<211> LENGTH: 56
<212> TYPE: DNA
<213> ORGANISM: Artificial Sequence
<220> FEATURE:
<223> OTHER INFORMATION: Sense primer for amplification of ptxD coding
      sequence of Pseudomonas stutzeri

<400> SEQUENCE: 22
ggggacaagt ttgtacaaaa aagcaggcta aatgctgccg aaactcgtta taactc         56

<210> SEQ ID NO 23
<211> LENGTH: 48
<212> TYPE: DNA
<213> ORGANISM: Artificial Sequence
<220> FEATURE:
<223> OTHER INFORMATION: Antisense primer for amplification of ptxD
      coding sequence of Pseudomonas stutzeri

```
<400> SEQUENCE: 23
ggggaccact ttgtacaaga aagctgggta tcaacatgcg gcaggctc                    48
```

TRANSGENIC PLANTS AND FUNGI CAPABLE OF METABOLIZING PHOSPHITE AS A SOURCE OF PHOSPHORUS

CROSS-REFERENCES TO PRIORITY APPLICATIONS

This application is a continuation of U.S. patent application Ser. No. 13/560,618, filed Jul. 27, 2012, now U.S. Pat. No. 10,851,386, which in turn is a continuation of U.S. patent application Ser. No. 13/130,285, filed May 19, 2011, which in turn claims priority under 35 U.S.C. § 371 to PCT Application Serial No. PCT/IB2009/007741, filed Nov. 19, 2009, which in turn claims priority to U.S. Provisional Patent Application Ser. No. 61/199,784, filed Nov. 19, 2008.

Each of these priority documents is incorporated herein by reference in its entirety for all purposes.

INTRODUCTION

Phosphorus is an essential element for plant and fungal growth. This element, in oxidized form, is incorporated into many of the biomolecules in a plant or fungal cell, such as to provide genetic material, membranes, and molecular messengers, among others.

Inorganic phosphate (Pi) is the primary source of phosphorus for plants. Accordingly, phosphate-based fertilizers offer a cheap and widely used approach to enhancing plant growth. However, phosphate-based fertilizers come from a non-renewable resource that has been projected to be depleted in the next seventy to one hundred years, or sooner if the usage rate increases faster than expected.

The phosphate-based fertilizers common to modern agriculture generally cannot be used efficiently by cultivated plants, due to several important factors. First, phosphate is highly reactive and can form insoluble complexes with many soil components, which reduces the amount of available phosphorus. Second, soil microorganisms can rapidly convert phosphate into organic molecules that generally cannot be metabolized efficiently by plants, which reduces the amount of available phosphorus further. Third, growth of weeds can be stimulated by phosphate-based fertilizers, which not only reduces the amount of available phosphorus still further but which also can encourage the weeds to compete with the cultivated plants for space and other nutrients. Losses due to the conversion of phosphate into inorganic and organic forms that are not readily available for plant uptake and utilization, and competition from weeds, implies the use of excessive amounts of phosphate fertilizer, which not only increases production costs but also causes severe ecological problems. Therefore, there is an urgent need to reduce the amount of phosphate fertilizer used in agriculture.

A reduced form of phosphate, phosphite (Phi), is also used in cultivation of plants. It has been shown that treatment with phosphite can increase plant production (as measured by fruit size and biomass) in avocado and citrus fruits. Phosphite may be transported into plants using the same transport system as phosphate and may accumulate in plant tissues for extended periods of time. However, there apparently are no reports of any enzymes in plants that can metabolize phosphite into phosphate, the primary source of phosphorus in plants. Moreover, even during phosphate starvation, phosphite apparently cannot satisfy the phosphorus nutritional requirements of the plant. Accordingly, in spite of similarities to phosphate, phosphite is a form of phosphorus that generally cannot be metabolized directly by plants, and thus is not a plant nutrient. Nevertheless, phosphite "fertilizers" are sold commercially, even though there appears be no proof or even an indication in the scientific literature that plants can assimilate phosphite.

Phosphite can promote plant growth indirectly. For example, phosphite is used as an anti-fungal agent (a fungicide) on cultivated plants. Phosphite is thought to prevent diseases caused by oomycetes (water molds) on such diverse plants as potato, tobacco, avocado, and papaya, among others. Phosphite thus may promote plant growth, not directly as a plant nutrient, but by protecting plants from fungal pathogens that would otherwise affect plant growth. Nevertheless, phosphite-based fungicides often are labeled as fertilizers. This mislabeling may be encouraged by government regulations that make the approval process shorter and less complex if manufacturers characterize fungicides as fertilizers.

The proposed mechanisms for phosphite acting as a fungicide are manifold. For example, phosphite may act on fungi by inhibiting phosphorylation reactions through an increment in the accumulation of inorganic pyrophosphate (PPi), which in turn can interrupt phosphate pathways that are metabolically critical. Alternatively, or in addition, phosphite may induce a natural defense response in plants. In any event, the efficacy of phosphite as a fungicide may be influenced by several factors, including environment, type of pathogen, type of plant, and concentration.

The concentration of phosphite in contact with plants may be a critical factor for phosphite effectiveness because too much phosphite can be toxic to plants. In particular, phosphite may compete with phosphate for entry into plant cells, since phosphite may be transported into plants via the phosphate transport system. Phosphite toxicity thus may be due to (1) reduced assimilation of phosphate by plants, in combination with (2) an inability to use phosphite as a source of phosphorus by oxidation to phosphate, which causes phosphite accumulation in the plants. Also, phosphite may be sensed in plants as phosphate, which prevents the plants from inducing a phosphorus salvage pathway that promotes plant survival under conditions of low phosphate. Phosphite toxicity affects such diverse plants as *Brassica nigra, Allium cepa* (onion), *Zea mays* L. (corn), and *Arabidopsis thaliana*. Accordingly, the exposure of plants to phosphite may need to be controlled very carefully. Therefore, a better system is needed for exploiting the benefits of phosphite to plants while reducing its drawbacks.

Generation of transgenic plants has been instrumental in creating improved agricultural systems. At least four selection systems have been established for identifying transgenic plants by selective growth. Each selection system is based on resistance to an antibiotic (kanamycin or hygromycin) or an herbicide (glyphosate or phosphinothricin). However, each selection system has disadvantages. For example, each selection system can have problems with toxicity. Also, selection with antibiotics may be inefficient since plants can have alternate resistance mechanisms. Furthermore, except for the selection system using phosphinothricin, none of the selection systems provides a "universal" selectable marker for most or all plants. Therefore, a new selectable marker is needed for use in generating transgenic plants.

SUMMARY

The present disclosure provides a system, including methods and compositions, for making and using transgenic plants and/or transgenic fungi that metabolize phosphite as a source of phosphorus for supporting growth.

BRIEF DESCRIPTION OF THE DRAWINGS

FIG. 5 is a schematic diagram of a portion of a strategy followed to create the chimeric gene of FIG. 4, in accordance with aspects of the present disclosure.

DETAILED DESCRIPTION

Figure 1:
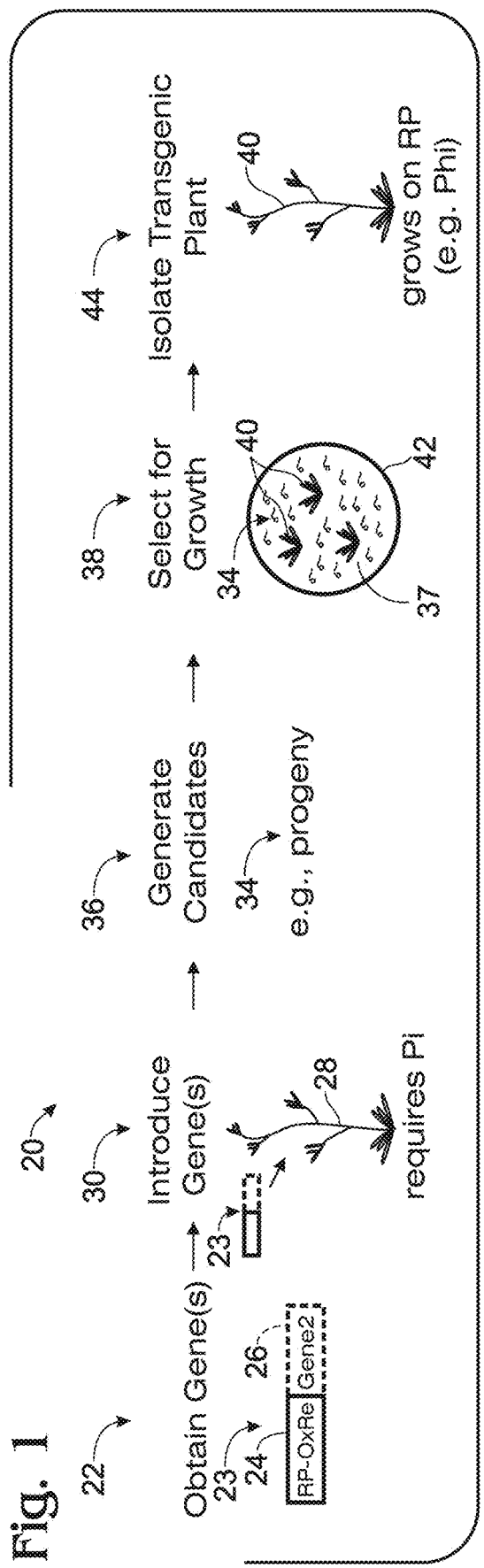
FIG. 1 is a schematic flowchart of an exemplary method of (i) making a transgenic plant (or fungus) that is capable of metabolizing a reduced form of phosphorus, such as phosphite, as a source of phosphorus for supporting growth, and/or (ii) using, as a selectable marker, a nucleic acid that confers a capability to metabolize a reduced form of phosphorus, such as phosphite, as a source of phosphorus for supporting growth, in accordance with aspects of the present disclosure.

The present disclosure provides a system, including methods and compositions, for making and using transgenic plants and/or transgenic fungi that metabolize phosphite as a source of phosphorus for supporting growth. The plants and/or fungi optionally also may metabolize hypophosphite as a source of phosphorus. The system disclosed herein may substantially change the way a more reduced form of phosphorus (relative to phosphate), such as phosphite, is utilized as a fertilizer and/or fungicide. The system also may provide a new selectable marker for use in generating transgenic plants and/or fungi. The system further may substantially change the way at least one reduced form of phosphorus is removed from waste water, such as industrial/municipal effluents.

A nucleic acid is provided. The nucleic acid may be used for generating a transgenic plant and/or fungus. The nucleic acid, which may be termed a construct, may comprise at least one chimeric gene that confers on a plant cell and/or fungal cell a capability to metabolize at least one reduced form of phosphorus to phosphate. In some embodiments, the nucleic acid may comprise a gene that expresses a phosphite dehydrogenase enzyme, a gene that expresses a hypophosphite dehydrogenase enzyme, or both.

The nucleic acid may comprise a chimeric gene including a coding region and a transcription promoter. The coding region may encode a phosphite dehydrogenase enzyme, such as PtxD from *Pseudomonas stutzeri*, a homolog of PtxD from the same or another bacterial species, or a derivative of either, among others. In some examples, the coding region may be at least 80%, 90%, or 95% (or completely) identical to the ptxD coding sequence of *Pseudomonas stutzeri*. The promoter may be functional in plants, fungi, or both and may be operatively linked to the coding region. The promoter may be heterologous with respect to the coding region. The chimeric gene may be capable of promoting sufficient expression of the enzyme, in a plant or fungal cell containing the nucleic acid, to confer an ability on the cell to metabolize phosphite (Phi) as a phosphorus source for supporting growth, thereby enabling growth of the cell without an external source of phosphate (Pi). The promoter may (or may not) be a plant promoter or a viral promoter of a plant virus and may be capable of promoting the sufficient expression of the enzyme in a plant cell. For example, the promoter, such as a promoter obtained from the PLDZ2 gene of *Arabidopsis thaliana*, may be inducible by low phosphate availability. Alternatively, or in addition, the promoter may be a root-specific promoter. In other cases, the promoter may be constitutive and may correspond to the 35S promoter of Cauliflower Mosaic Virus. In some embodiments, the nucleic acid may include a transcription terminator that is functional in the plant cell and/or fungal cell and that is operatively linked to the promoter and coding region. In some embodiments, the promoter may be a fungal promoter capable of promoting the sufficient expression of the enzyme in a fungal cell.

The nucleic acid may provide expression of one or more polypeptides that metabolize at least one reduced form of phosphorus to phosphate, to enable a transgenic plant (or fungus) to use a reduced form of phosphorus as a nutrient. The expression of the one or more polypeptides may be heritable. For example, the nucleic acid may be integrated into the genome of the plant (or fungus). Furthermore, the expression of at least one of the polypeptides may be under control of a constitutive promoter or an inducible promoter (e.g., inducible by low phosphate, such as by use of a promoter from a PLDZ2 gene of *Arabidopsis* or a plant AtPT1 gene for a high affinity phosphate transporter), under control of a tissue-specific promoter (e.g., leaf-specific or root-specific), or a combination thereof, among others.

A plant cell or a fungal cell is provided that expresses a phosphite dehydrogenase enzyme from a chimeric gene. The cell may be isolated from other cells or may be associated with other cells in a multi-cellular structure (e.g., a plant or a mycelium). The cell may (or may not) also express a hypophosphite dehydrogenase enzyme from a chimeric gene. Accordingly, the cell may metabolize phosphite, hypophosphite, or both, as a phosphorus source for supporting growth. In some embodiments, the cell may be a plant cell and expression of the phosphite dehydrogenase enzyme, the hypophosphite dehydrogenase enzyme (if present), or both may be controlled by a root-specific promoter. The plant cell may be from any suitable species. For example, the plant cell may be a eukaryotic algal cell, such as a *Chlamydomonas* cell. In other cases, the plant cell may be from a species of vascular plant. In some embodiments, the cell may be a fungal cell that belongs to a species of *Trichoderma* or that belongs to a mycorrhizal species of fungus capable of forming a symbiotic relationship with a plant.

A transgenic plant (or plant part) is provided that expresses a phosphite dehydrogenase enzyme, and, optionally, a hypophosphite dehydrogenase enzyme from one or more chimeric genes. The plant may, through expression of the enzyme(s), metabolize phosphite and/or hypophosphite as a source of phosphorus for supporting growth. The plant may be a vascular plant, such as crop plant, for example, a species of crop plant selected from the group consisting of maize, soybean, rice, potatoes, tomatoes, sugarcane, and wheat. A seed that germinates to produce the transgenic plant also is provided.

A method of reducing fungal infections in plants is provided. A plurality of fungal cells may be applied to a seed form of plants, the plants themselves, soil in which the plants are or will be disposed, or a combination thereof. The fungal cells may express a phosphite dehydrogenase enzyme from a chimeric gene and may belong to a species of *Trichoderma*.

A plant associated with a plurality of fungal cells to form mycorrhizae is provided. The fungal cells may express a phosphite dehydrogenase enzyme from a chimeric gene. The fungal cells may render the plant capable of growth on phosphite (and/or hypophosphite) as a phosphorus source by oxidizing phosphite to phosphate.

A method is provided of fertilizing a crop plant using hypophosphite and/or phosphite as a phosphorus source for supporting growth. The crop plant may express a phosphite dehydrogenase enzyme, a hypophosphite dehydrogenase enzyme, or both. Alternatively, or in addition, the crop plant may form mycorrhizae with a plurality of fungal cells expressing a phosphite dehydrogenase enzyme, a hypophosphite dehydrogenase enzyme, or both. At least one reduced form of phosphorus, such as phosphite and/or hypophosphite, may be applied to the plant and/or to soil adjacent the plant, such that the reduced form is metabolized to phosphate by the plant and/or the mycorrhizae to support growth and productivity of the plant.

A method is provided of treating liquid waste (e.g., an effluent) to lower its content of reduced phosphorus. Contact is created between (i) water containing hypophosphite and/or phosphite as a contaminant and (ii) a plurality of plant cells and/or fungal cells expressing a phosphite dehydrogenase enzyme, a hypophosphite dehydrogenase enzyme, or both, such that at least a portion of the hypophosphite and/or phosphite is oxidized to phosphite and/or phosphate. In some cases, the contact may be created between the water and a plurality of vascular plants expressing one or both of the enzymes. The method may provide a bioremediation system for rivers, reservoirs, soils, holding tanks, and the like that are contaminated due to industrial manufacturing. For example, phosphite is a common polluting agent in rivers and lakes near industrial sites, such as manufacturers of optical discs (e.g., DVDs and CDs) that use hypophosphite to reduce metal ions in chemical plating processes. Transgenic plants and/or fungi disclosed herein thus may help remove hypophosphite and/or phosphite from contaminated water by taking up and converting the hypophosphite and/or phosphite into phosphate. Use of plants and/or fungi may be more efficient than using a bacterial-based system.

A method is provided of utilizing a coding sequence for a phosphite dehydrogenase as a selectable marker for production of a transgenic plant. The method may be used to obtain a plant transformed with a nucleic acid encoding a phosphite dehydrogenase enzyme that is expressible from the nucleic acid as a selectable marker. Plant cells and a composition including the nucleic acid may be contacted under conditions that promote introduction of the nucleic acid into the plant cells. The plant cells may be cultured in a medium containing phosphite as a primary or exclusive phosphorus source for growth of the plant cells. Selection may be performed of transformed plant cells produced by the steps of contacting and culturing and that express the phosphite dehydrogenase enzyme as evidenced by growth in the medium. At least a portion of the transformed plant cells may be regenerated into a transgenic plant.

The transgenic plants disclosed herein may provide substantial benefits. For example, in some cases, the plants may metabolize phosphite using NAD+ as an electron acceptor, to generate NADH and phosphate, which are both useful molecules for the plant. The transgenic plants also or alternatively may provide development of a new agricultural system based on phosphite. Phosphite may be less reactive in the soil than phosphate and therefore may create fewer insoluble compounds that the plant cannot utilize. Also, since most soil microorganisms are unable to metabolize phosphite, less of the phosphite (relative to phosphate) is converted into organic forms that plants cannot utilize. Furthermore, phosphite may have less impact on the bacterial ecosystem around the plants relative to phosphate. Competition from weeds also may be reduced substantially since the weeds should not be able to utilize phosphite. The use of phosphite thus should decrease fertilizer costs and reduce the negative impact of fertilizer on the environment.

The transgenic plants disclosed herein also may offer increased effectiveness of phosphite as a fungicide, while acting as a fertilizer on the transgenic plants. When used as a fungicide on non-transgenic plants, phosphite generally needs to be used very carefully, to avoid plant toxicity. However, in the transgenic plants disclosed herein, phosphite may be metabolized by the plant to become non-toxic.

The system disclosed herein may provide substantial advantages for generating transgenic plants. A selectable marker of the system may function at least substantially universally in plants. Furthermore, the selective agent (e.g., hypophosphite or phosphite) may be nontoxic for transgenic plants, since the reaction products may be innocuous (e.g., NADH and phosphate), and also may be less expensive than in other selection schemes.

Further aspects of the present disclosure are provided in the following sections: (I) definitions, (II) generation of transgenic plants and fungi, (III) use of transgenic plants and fungi, and (IV) examples.

I. Definitions

The various terms used in the present disclosure generally each have a meaning recognized by those skilled in the art, consistent with the context in which each term is used. However, the following terms may have additional and/or alternative meanings, as described below.

Plant—a member of the Plantae kingdom of eukaryotic organisms, which may be described as a tree, bush, grass, shrub, herb, vine, fern, moss, a eukaryotic alga, or a combination thereof, among others. A plant typically possesses cellulose cell walls and is capable of carrying out photosynthesis. The plant may be a vascular plant. In some embodiments, the plant may be an annual or a perennial. The plant may be a flowering plant, such as a monocotyledon or a dicotyledon. In some embodiments, the plant may produce a grain, tuber, fruit, vegetable, nut, seed, fiber, or a combination thereof, among others. Furthermore, the plant may be a crop plant, which may be cultivated in a field. Exemplary crop plants that may be suitable for generation of transgenic plants according to the present disclosure include tobacco (e.g., *N. tabacum*), potato, maize, rice, wheat, alfalfa, soybean, tomato, sugarcane, and the like.

Plant part—any portion of a plant that is less than a whole plant and that includes at least one plant cell. A plant part thus may be a plant tissue, such as leaf tissue, root tissue, stem tissue, shoot tissue, callus tissue, flower tissue, or any combination thereof, among others. A plant part may be an isolated plant cell or a colony or set of plant cells. A plant cell may be a protoplast or may include a cell wall, among others.

Transgenic—comprising a nucleic acid construct. The construct may be integrated into an organism's (and/or cell's) genome (e.g., nuclear or plastid genome), in any subset or at least substantially all of the cells of the organism. For example, the construct may be present in a plant's germline. Accordingly, the construct may be heritable, that is, inherited by at least one or more members, or at least substantially all members, of a succeeding generation of the organism, or in descendants of a cell. A plant or fungus (or plant or fungal part (e.g., a cell)) that is "transformed" with a construct has been modified to contain the construct in the current generation or in any preceding generation(s) of the plant or fungus (or plant or fungal part). A transgenic plant may be provided by a seed that germinates to form the transgenic plant. Also, a transgenic plant may produce one or more seeds that germinate to produce transgenic progeny plants.

Nucleic acid—a compound comprising a chain of nucleotides. The chain may be composed of any suitable number of nucleotides, such as at least about 10, 100, or 1000, among others. A nucleic acid may be termed a polynucleotide, and may, for example, be single-stranded, double-stranded, or a combination thereof.

Gene—a nucleic acid or segment thereof that provides an expressible unit for expression of a polypeptide and/or a functional RNA (e.g., a messenger RNA, an interfering RNA, or an enzymatic RNA, among others). A gene thus may include (a) a coding region (also termed a coding sequence, which may be continuous or interrupted (such as by one or more introns)) to define the sequence of the polypeptide and/or functional RNA, (b) at least one transcription promoter (also termed a promoter sequence) and, (c) optionally, at least one transcription terminator (also termed a termination sequence), with the transcription promoter and the transcription terminator operatively linked to the coding region. A gene optionally may include one or more other control regions and/or untranslated regions, such as at least one 5' untranslated region, 3' untranslated region, intron, or any combination thereof, among others.

Promoter—a nucleic acid region that controls (i.e., promotes, regulates, and/or drives) transcription of a gene to produce a primary transcript and/or a messenger RNA. A promoter may operate, for example, by determining, at least in part, the rate of transcriptional initiation of a gene by RNA polymerase. The promoter also or alternatively may determine the rate of transcriptional elongation after transcription is initiated. The promoter may be functional in plants and/or fungi and thus may be a plant promoter and/or a fungal promoter.

Chimeric gene—a gene with sequence elements, such as a transcription promoter and a coding region, that are heterologous with respect to one another. The term "heterologous" means that the sequence elements (e.g., the promoter and coding region) originate and/or are derived from respective distinct sources, such as distinct species of organisms. A chimeric gene also may comprise a transcription terminator, which may originate from a source distinct from the coding region, and from the same source as, or a source distinct from, the promoter. Exemplary terminators that may be used in the chimeric genes include the 35S terminator of Cauliflower Mosaic Virus, the nopaline synthase terminator of *Agrobacterium tumefaciens*, or the like.

Construct—a nucleic acid created, at least in part, using techniques of genetic engineering. A construct thus may be termed a nucleic acid construct.

Expression—a process by which a product, namely, an RNA and/or a polypeptide, is formed from information provided by a nucleic acid and/or gene, generally in the form of DNA. Accordingly, the nucleic acid/gene may be expressed to form an RNA and/or polypeptide, which means that the RNA and/or polypeptide is expressed from the nucleic acid/gene.

Reduced forms of phosphorus—any phosphorus-containing compounds and/or ions in which phosphorus has an oxidation state of less than +5, such as +3 or +1. Accordingly, reduced forms of phosphorus may, for example, include phosphite and hypophosphite, among others. A reduced form of phosphorus may be abbreviated "RP."

Phosphate—phosphoric acid ($H_3PO_4$), its dibasic form ($H_2PO_4^{1-}$), its monobasic form ($HPO_4^{2-}$), its triply ionized form ($PO_4^{3-}$), or any combination thereof. Phosphate may be provided as any suitable phosphate compound or combination of phosphate compounds. Exemplary forms of phosphate include phosphate salts of sodium, potassium, lithium, rubidium, cesium, ammonium, calcium, or magnesium, or any combination thereof, among others. In phosphate, four oxygens are bonded directly to a phosphorus atom. Phosphate also or alternatively may be called "orthophosphate" and/or "inorganic phosphate" and may be abbreviated as "Pi." Phosphate is distinct from "organophosphate," which is an organic version of phosphate in which one or more of the phosphate oxygens are bonded to organic moieties, generally to form a phosphate ester.

Phosphite—phosphorous acid ($H_3PO_3$), its conjugate base/singly ionized form ($H_2PO_3^{1-}$), or its doubly ionized form ($HPO_3^{2-}$), or any combination thereof. In phosphite, three oxygens and one hydrogen are bonded directly to a phosphorus atom. Phosphite may be provided as any suitable phosphite compound or combination of phosphite compounds. Exemplary forms of phosphite include phosphite salts of sodium, potassium, lithium, rubidium, cesium, ammonium, calcium, or magnesium, or any combination thereof, among others. Phosphite can be oxidized to phosphate. Phosphite also or alternatively may be called "inorganic phosphite" and may be abbreviated as "Phi." Phosphite is distinct from "organophosphite," which is an organic version of phosphite in which one or more of the phosphite oxygens are bonded to organic moieties, generally to form a phosphite ester.

Hypophosphite—hypophosphorous acid ($H_3PO_2$) and/or its conjugate base ($H_2PO_2^-$), which may be provided as any suitable hypophosphite compound or combination of hypophosphite compounds. In hypophosphite, two oxygens and two hydrogens are bonded directly to a phosphorus atom. Exemplary forms of hypophosphite include hypophosphite salts of sodium, potassium, lithium, rubidium, cesium, ammonium, or a combination thereof, among others. Hypophosphite can be oxidized to phosphite and/or to phosphate. Hypophosphite also or alternatively may be called "inorganic hypophosphite" and may be abbreviated as "Hphi."

Nutrient—any substance that is metabolized to promote growth and reproduction, and/or is required for survival.

Fertilizer—any composition that includes one or more nutrients for plants (and/or fungi associated with the plants).

External Source—a supply that is outside of a plant and accessible to the plant, generally by contact with the plant. Exemplary external sources that may be suitable for the transgenic plants described herein may include an external source of phosphorus, an external source of phosphate, or an external source of reduced phosphorus, among others.

Selectable Marker—a construct or segment thereof and/or a gene that confers a growth advantage on a plant or plant part (and/or a fungus and/or fungal cell) that contains the construct/gene, when growth of the plant or plant part (and/or fungus and/or fungal cell) is tested by contact with a suitable culture medium.

Effluent—water carrying and/or mixed with waste material. An effluent may or may not be flowing. An exemplary effluent may, for example, be industrial refuse and/or sewage, which may be combined with a larger body of water, such as a stream, river, pond, lake, swamp, wetland, or the like.

Remediation—any process that modifies water (e.g., waste water and/or an effluent) to a more desired composition, such as to make the water less toxic, more environmental friendly, in better conformation with government standards, etc.

Enzyme that oxidizes a reduced form of phosphorus—an enzyme that catalyzes or promotes oxidation of a reduced form of phosphorus (e.g., with an oxidation state of +1 or +3) to a more oxidized state (e.g., +1 to +3, +1 to +5, and/or +3 to +5). For example, the enzyme may oxidize hypophosphite to phosphite, phosphite to phosphate, and/or hypophosphite to phosphate, among others. For convenience, the enzyme may be termed an "oxidase," since it catalyzes/promotes an oxidation reaction, or may be called a "phosphorus oxidoreductase" or "enzyme of reduced phosphorus metabolism," and may be abbreviated, for convenience herein, as "RP-OxRe." Exemplary enzymes that oxidize a reduced form of phosphorus may include a phosphite dehydrogenase enzyme (which may, for example, be called NAD:phosphite oxidoreductase, phosphonate dehydrogenase, NAD-dependent phosphite dehydrogenase, or the like), a hypophosphite dehydrogenase (e.g., hypophosphite:2-oxoglutarate oxidoreductase), or the like. The enzyme may oxidize a reduced form of phosphorus using any suitable cofactor(s), coenzyme(s), and/or substrate(s) present in and/or near a cell. Furthermore, the enzyme may originate and/or be derived from bacteria, fungi, plants, or animals.

Phosphite dehydrogenase enzyme—an enzyme that catalyzes oxidation of phosphite to phosphate. The enzyme generally catalyzes the oxidation with sufficient efficiency to enable growth of a plant cell and/or fungal cell in the presence of phosphite as a phosphorus source to support growth. The enzyme may be of bacterial origin. The enzyme may be a PtxD polypeptide (i.e., PtxD or PtxD-like), which is any polypeptide that is capable of catalyzing oxidation of phosphite to phosphate and that is (a) at least 90%, 95%, or completely identical to PtxD (SEQ ID NO:1; GenBank: AAC71709.1) of *Pseudomonas stutzeri* WM 88, (b) a derivative of PtxD of SEQ ID NO:1, (c) a homolog (i.e., a paralog or ortholog) of PtxD (SEQ ID NO:1) from the same or a different bacterial species, or (d) a derivative of (c). Homologs of PtxD (SEQ ID NO:1) have substantial similarity to PtxD of *Pseudomonas stutzeri*, which may, for example, be determined by the blastp algorithm (e.g., program BLASTP 2.2.18+), as described in the following two references, which are incorporated herein by reference: Stephen F. Altschul, et al. (1997), "Gapped BLAST and PSI-BLAST: a new generation of protein database search programs," Constructs Res. 25:3389-3402; and Stephen F. Altschul et al. (2005) "Protein database searches using compositionally adjusted substitution matrices," FEBS J. 272:5101-5109. Examples of substantial similarity include at least 50%, 60%, 70%, or 80% sequence identity, a similarity score of at least 200 or 250, and/or an E-Value of less than 1e-40, 1e-60, or 1e-80, among others, using the blastp algorithm, with optimal alignment and, if needed, introduction of gaps.

Exemplary homologs of PtxD of *Pseudomonas stutzeri* may be provided by *Acinetobacter radioresistens* SK82 (SEQ ID NO:2; GenBank EET83888.1); *Alcaligenes faecalis* (SEQ ID NO:3; GenBank AAT12779.1); *Cyanothece* sp. CCY0110 (SEQ ID NO:4; GenBank EAZ89932.1); *Gallionella ferruginea* (SEQ ID NO:5; GenBank EES62080.1); *Janthinobacterium* sp. Marseille (SEQ ID NO:6; GenBank ABR91484.1); *Klebsiella pneumoniae* (SEQ ID NO. 7; Genbank ABR80271.1); *Marinobacter algicola* (SEQ ID NO:8; GenBank EDM49754.1); *Methylobacterium extorquens* (SEQ ID NO:9; NCBI YP_003066079.1); *Nostoc* sp. PCC 7120 (SEQ ID NO:10; GenBank BAB77417.1); *Oxalobacter formigenes* (SEQ ID NO. 11; NCBI ZP_04579760.1); *Streptomyces sviceus* (SEQ ID NO:12; GenBank EDY59675.1); *Thioalkalivibrio* sp. HL-EbGR7 (SEQ ID NO:13; GenBank ACL72000.1); and *Xanthobacter flavus* (SEQ ID NO:14; GenBank ABG73582.1), among others. Further aspects of PtxD homologs are described in U.S. Patent Application Publication No. 2004/0091985 ("the '985 publication") to Metcalf et al., which is incorporated herein by reference. The phosphite dehydrogenase may have an amino acid sequence with at least 50%, 60%, 80%, 90% or 95% or 100% sequence identity to one or more of SEQ ID NOS:1-14.

Exemplary derivatives of PtxD of *Pseudomonas stutzeri* that may be suitable are described in the '985 publication and in U.S. Pat. No. 7,402,419 to Zhao et al., which is incorporated herein by reference. The derivatives may provide, for example, altered cofactor affinity/specificity and/or altered thermostability.

The phosphite dehydrogenase enzyme may contain a sequence region with sequence similarity or identity to any one or any combination of the following consensus motifs: an NAD-binding motif having a consensus sequence of VGILGMGAIG (SEQ ID NO:15); a conserved signature sequence for the D-isomer specific 2-hydroxyacid family with a consensus sequence of XPGALLVNPCRGSVVD (SEQ ID NO:16), where X is K or R, or a shorter consensus sequence within SEQ ID NO:16 of RGSVVD (SEQ ID NO:17); and/or a motif that may enable hydrogenases to use phosphite as a substrate, with a general consensus of GWQPQFYGTGL (SEQ ID NO:18), but that can be better defined as $GWX_1PX_2X_3YX_4X_5GL$ (SEQ ID NO. 19), where $X_1$ is R, Q, T, or K, $X_2$ is A, V, Q, R, K, H, or E, $X_3$ is L or F, $X_4$ is G, F, or S, and $X_5$ is T, R, M, L, A, or S. Further aspects of consensus sequences found by comparison of PtxD and PtxD homologs are described in U.S. Patent Application Publication No. 2004/0091985 to Metcalf et al., which is incorporated herein by reference.

A phosphite dehydrogenase enzyme may (or may not) be a NAD-dependent enzyme with high specificity for phosphite as a substrate (e.g., Km ~50 μM) and/or with a molecular weight of about 36 kilodaltons. The dehydrogenase enzyme may, but is not required to, act as a homodimer, and/or have an optimum activity at 35° C. and/or a pH of about 7.25-7.75.

Hypophosphite dehydrogenase—an enzyme that catalyzes oxidation of hypophosphite to phosphite. The enzyme may, for example, be a bacterial enzyme, such as HtxA from *Pseudomonas stutzeri* WM 88 (SEQ ID NO:20; GenBank AAC71711.1) or *Alcaligenes faecalis* (GenBank AAT12775.1).

An HtxA polypeptide may, but is not required to, be a Fe-dependent enzyme with high specificity for hypophosphite as a substrate (e.g., Km ~0.54-0.62 mM) and/or with a molecular weight of about 32 kilodaltons. The HtxA polypeptide may, but is not required to, act as a homodimer, and/or to have an optimum activity at 27° C. and/or a pH of about 7.0.

ptxD or htxA coding region—a sequence encoding a PtxD polypeptide (i.e., a phosphite dehydrogenase enzyme) or an HtxA polypeptide (i.e., a hypophosphite dehydrogenase enzyme), respectively. An exemplary ptxD coding region is provided by ptxD of *Pseudomonas stutzeri* (SEQ ID NO:21; GenBank AF061070.1). In other examples, a ptxD-like coding region with at least 80% or 90% sequence identity to SEQ ID NO:21 may be utilized. In other examples, a coding region that encodes a polypeptide with at least 50%, 60%, 80%, 90%, 95% or complete identity to one or more of the polypeptides of SEQ ID NOS:1-14 may be utilized.

II. Generation of Transgenic Plants and Fungi

The present disclosure provides methods of making transgenic plants and transgenic fungi that have a modified metabolism of phosphorus. The methods may be used to create, as a primary goal, transgenic plants and/or fungi (or at least one plant or fungal cell) carrying a nucleic acid construct encoding an enzyme of phosphorus oxidation, such as for better growth on a phosphite and/or hypophosphite fertilizer in agriculture. Alternatively, or in addition, the methods may be used to create, as a primary goal, transgenic plants and/or fungi carrying a construct including another gene of interest, with the construct also including a gene encoding an enzyme of phosphorus oxidation acting as a selectable marker to facilitate identification and/or isolation of the transgenic plants or fungi. The method steps disclosed in this section and elsewhere in the present disclosure may be performed in any suitable combination, in any suitable order, and repeated any suitable number of times.

FIG. 1 shows a schematic flowchart of an exemplary method 20 of (i) making a transgenic plant (and/or fungus) that metabolizes at least one reduced form of phosphorus ("RP") to phosphate and/or (ii) using, as a selectable marker, a nucleic acid that confers a capability to metabolize a reduced form of phosphorus to phosphate.

At least one construct (or nucleic acid) may be obtained, as indicated at 22. The at least one construct 23 may include at least one first gene 24, which may be at least one chimeric gene encoding at least one enzyme ("RP-OxRe"), such as a phosphite dehydrogenase, that catalyzes oxidation of a reduced form of phosphorus, such as oxidation of phosphite to phosphate. Construct 23 also may include at least one second gene 26 ("Gene2"), which also may (or may not) be a chimeric gene. In some embodiments, the at least one first gene may be a pair of genes encoding at least two distinct polypeptides that each catalyze oxidation of at least one reduced form of phosphorus. The at least two polypeptides may act to oxidize phosphorus substrates in series (e.g., catalyzing oxidation of hypophosphite to phosphite with a first polypeptide and then catalyzing oxidation of phosphite to phosphate with a second polypeptide). In some examples, the at least one second gene may include a selectable marker for use in plants and/or fungi and/or may include a gene(s) of primary interest, among others. First gene 24 and second gene 26 may be linked, such as being present in the same polynucleotide, or may be present on respective discrete polynucleotides. Each gene may be constructed, at least in part, outside of plants, such as in vitro and/or in a microorganism (e.g., bacteria, yeast, etc.). Furthermore, each gene may be capable of expression in plants, fungi, or both that contain the gene.

The at least one gene (24 and/or 26) may be introduced into at least one recipient plant 28 (or fungus), plant or fungal tissue, and/or plant or fungal cell, indicated at 30. The at least one plant, tissue, or cell, prior to introduction of the at least one gene, may at least substantially require phosphate as an external source of phosphorus for growth. In other words, the plant, tissue, or cell may be at least substantially unable to metabolize directly a reduced form of phosphorus (such as phosphite) as a nutrient.

Introduction of the at least one gene may be performed by contacting (a) the at least one plant/fungus, tissue, and/or cell and (b) a composition (a modifying agent) that includes a nucleic acid comprising the at least one gene, under conditions that encourage introduction of the nucleic acid into the plant, tissue, and/or cell. The step of contacting may be performed by any mechanism that creates contact between the at least one plant/fungus, tissue, and/or cell and the composition. The composition may, for example, include one or more polynucleotides containing the at least one gene, with the polynucleotides in and/or on a carrier. Exemplary carriers that may be suitable include biological cells (e.g., bacterial cells), plant viruses, inert particles, lipids (in micelles and/or liposomes), and/or the like. Exemplary contact created with a composition including the gene may include contacting a plant, plant tissue, or plant cells with a bacterium (e.g., an *Agrobacterium* species, such as *Agrobacterium tumefaciens* or *Agrobacterium rhizogenes*) carrying the at least one gene, or with one or more projectiles carrying the at least one gene (e.g., particles coated with a polynucleotide including the at least one gene and fired at the plant, tissue, or cell from a gene gun). More generally, introducing the at least one gene may be performed on a plant/fungus, plant or fungal tissue, and/or plant or fungal cells by infection, injection, particle bombardment, electroporation, cell fusion, lipofection, calcium-phosphate mediated transfection, any combination thereof, or the like.

Transgenic candidates 34 (also termed transformation candidates) may be generated, indicated at 36, by and/or after creating contact between the plant, tissue, and/or cells and the composition. The transgenic candidates may be the plant/fungus, tissue, and/or cells used for contacting, or may be derived from any later generation (i.e., progeny or division products) of the plant/fungus, tissue, and/or cells. In any event, the transgenic candidates may be seeds, plants, tissues, explants, isolated cells, cell colonies/aggregates, and/or the like.

Selection for growth (i.e., a growth advantage) of transgenic candidates 34 in a selective medium 37 may be performed, indicated at 38. Candidates 34 that possess a growth advantage on the selective medium, such as transgenic plants 40, generally are substantially larger than the other candidates. In other examples, the selection may be performed with transformed plant (or fungal) cells and may include culturing the plant (or fungal) cells in a selective medium. In these cases, culturing the cells may permit selection and/or isolation of one or more colonies of cells formed by the step of culturing. The colonies may be expressing an enzyme, such as a phosphite dehydrogenase, that oxidizes a reduced form of phosphorus, as evidenced by formation of the colony in the medium.

Any suitable selective medium 37 may be utilized according to a selectable marker provided by the at least one first gene and/or a selectable marker (second) gene that was introduced. For example, the selective medium may include a reduced form of phosphorus, such as hypophosphite and/or phosphite. The reduced form of phosphorus may be a primary external source of phosphorus and/or may be at least substantially the only phosphorus present in the medium, which means that the medium is at least substantially without phosphate (i.e., a low phosphate or no phosphate medium). Alternatively, or in addition, the selective medium may include another selective agent, such as hygromycin or phosphinothricin, if the selection for growth is based on second gene 26 (e.g., hph or bar) introduced into the plant/fungus, tissue, and/or cell. If the selection is based on second gene 26, additional tests (e.g., growth in phosphite-containing medium, PCR, Southern blot, etc.) may be performed to test for introduction of the at least one first gene encoding at least one RP-oxidoreductase. In any event, the medium may include or be predominantly liquid and may (or may not) include a matrix or substrate, such as a gel (e.g., agar, agarose, gelatin, etc.) or soil, among others.

Selection for growth may be performed in any suitable vessel 42 (and/or container) or may be performed without a vessel or container, such as in a field. Exemplary vessels that may be suitable are covered or uncovered and include single- or multi-well plates or dishes (e.g., Petri dishes), pots, trays, boxes, etc.

Transgenic plant 40 may be isolated, indicated at 44. Plant 40 may have a growth advantage conferred by nucleic acid 23 for growth on a reduced form of phosphorus, relative to a non-transgenic variety of the plant (e.g., plant 28) from which transgenic plant 40 was derived. Stated differently nucleic acid 23 may confer a capability to metabolize the reduced form of phosphorus as a nutrient. In some embodiments, transgenic plant 40 may be regenerated from transformed plant cells or tissue. For example, at least a portion of a colony of cells produced by cultivating the plant cells in a selective (e.g., phosphite) medium may be utilized to regenerate the transgenic plant. Further aspects of generating transgenic plants and fungi are described elsewhere in the present disclosure, such as in the Examples of Section IV.

Figure 2:
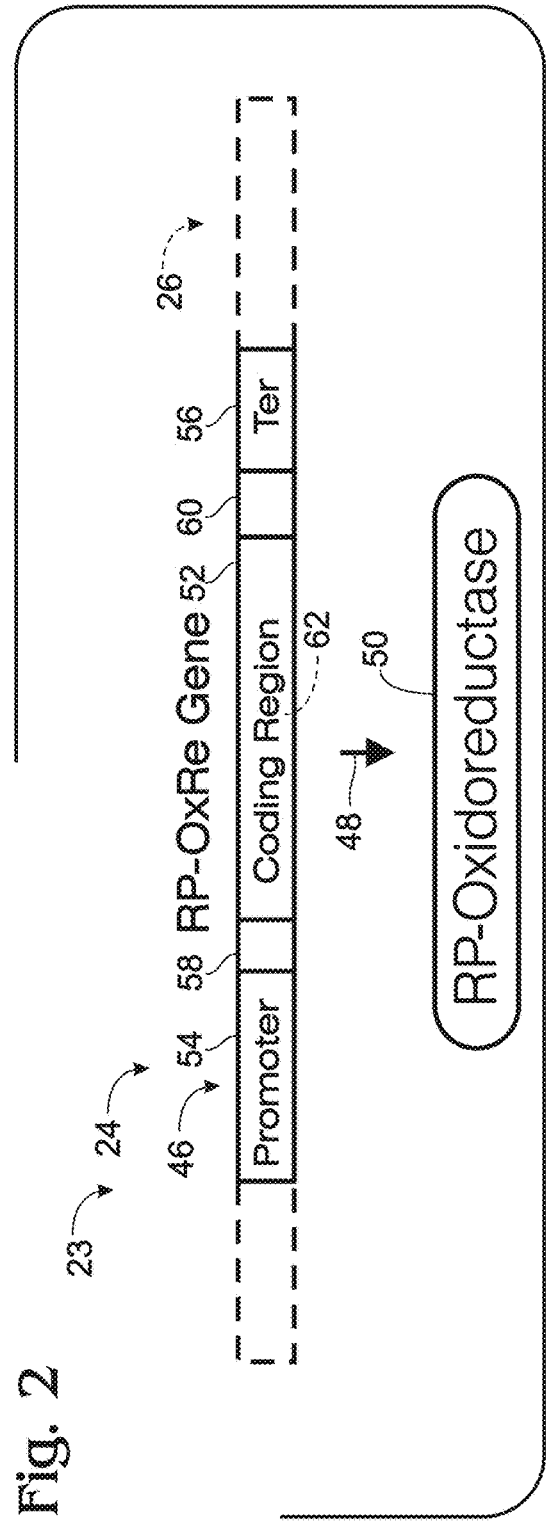
FIG. 2 is a schematic representation an exemplary nucleic acid for use in the method of FIG. 1, in accordance with aspects of the present disclosure.

FIG. 2 shows a schematic representation of nucleic acid 23 for use in method 20 (FIG. 1). Gene 24 may be termed an RP-OxRe gene 46 that expresses, indicated at 48, a reduced phosphorus oxidoreductase 50 (e.g., a phosphite dehydrogenase). Gene 24 includes a coding region 52 that encodes the oxidoreductase. Gene 24 also may include a transcription promoter 54 operatively linked to coding region 52, and a transcription terminator 56 operatively linked to coding region 52.

Promoter 54 and terminator 56 may be functional in plants and/or fungi. Accordingly, the promoter and/or the terminator may originate from a plant or fungus, or a virus or a bacteria that infects plants or fungi, among others. Exemplary promoters that may be suitable for use in plants include the 35S promoter of Cauliflower Mosaic Virus. Other promoters that may be suitable for use in plants include a PLDZ2 promoter from the Phospholipase DZ2 (PLDZ2) gene (Gene model AT3G05630.1; TAiR accession Gene:2078036) of *Arabidopsis thaliana*, which is inducible under conditions of low phosphate availability to the plant (Cruz-Ramírez et al., PNAS 2006, 103:6765-6770, the disclosure of which is incorporated herein by reference). Alternatively, or in addition, the promoter may be a root-specific promoter, such as the *Arabidopsis* Pht1;2 phosphate transporter gene (NCBI NM_123703.1; GeneID:834355) or the promoter of the MtPT1 gene or MtPT2 gene (GenBank: AF000354.1 and AF000355.1) of *Medicago truncatula* (Xiao, et al, Plant Biology, 2006, 8:439-449, the disclosure of which is incorporated herein by reference).

Furthermore, first gene 24 may include transcribed but untranslated regions, such as a 5' leader sequence and/or 5' untranslated region 58, a 3' untranslated region 60, and/or one or more introns 62. First gene 24 may be provided by nucleic acid 23 that includes any other suitable sequences, such as at least one second gene 26, replication control sequences for replication in bacteria or another non-plant species, a selectable marker for another species (e.g., bacteria), or any combination thereof, among others. In some embodiments, nucleic acid 23 may be any combination of linear or circular (i.e., a closed loop), at least mostly double-stranded or at least mostly single-stranded, and DNA or RNA.

Figure 3:
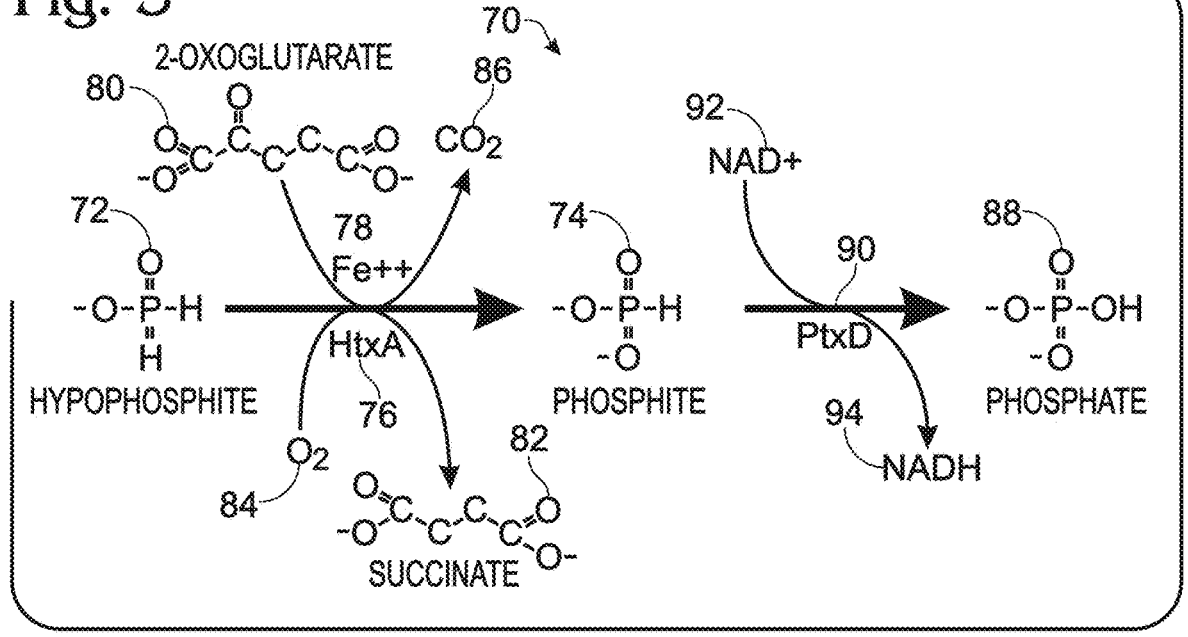
FIG. 3 is a proposed mechanism for oxidation of hypophosphite to phosphate in bacteria using enzymes expressed from the ptxD and htxA genes of *Pseudomonas stutzeri*, in accordance with aspects of the present disclosure.

FIG. 3 shows a proposed mechanism 70 for oxidation of hypophosphite to phosphate in bacteria catalyzed by enzymes expressed from ptxD and htxA genes. The proposed mechanism presented here is for illustration purposes only, and is not intended to limit the definition of any of the components shown, such as ptxD or htxA genes or PtxD or HtxA polypeptides, or limit the scope of the invention.

Mechanism 70 shows a hypophosphite ion 72 may be oxidized to a phosphite ion 74 by the action of an HtxA polypeptide 76 (hypophosphite:2-oxoglutarate dioxygenase) encoded by an htxA gene. HtxA polypeptide 76 may use $Fe^{2+}$ 78 as a cofactor and 2-oxoglutarate 80 as an electron donor. In addition, enzyme 76 may convert 2-oxoglutarate 80 to succinate 82, and molecular oxygen 84 to carbon dioxide 86.

Phosphite ion 74, in turn, may be oxidized to a phosphate ion 88 by the action of a PtxD polypeptide 90. Polypeptide 90 may use NAD+ 92 as an electron acceptor that is reduced to NADH 94.

III. Use of Transgenic Plants and Fungi

The transgenic plants disclosed herein may be used for any suitable purpose. Exemplary purposes include production of a commercial product (e.g., food, wood, pharmaceuticals, dyes, oils, lubricants, inks, rubber, cotton, fibers, biofuels, etc.), and/or water remediation. Water remediation, as used herein, generally includes any removal of pollution or at least one contaminant from a body of water and/or from soil that has contacted contaminated water.

A method of water remediation is provided. Any transgenic plant, fungi, or both disclosed herein may be used in the method. The method steps disclosed in the section and elsewhere in the present disclosure may be performed in any suitable order, in any suitable combination, with each step performed any suitable number of times.

One or more transgenic plants may be obtained. The transgenic plants may have been transformed, in the current generation or in any proceeding generation, with a construct that confers a capability of oxidizing at least one reduced form of phosphorus.

Obtaining the one or more transgenic plants may include any suitable procedures. For example, the step of obtaining may include introducing into the current generation or, more typically, an earlier generation of the transgenic plants, one or more constructs encoding one or more polypeptides that oxidize a reduced form of phosphorus to phosphate.

The one or more transgenic plants may be contacted with water to be remediated. Contacting plants to with water may include any combination of bringing the water to plants, bringing the plants to water, and germinating seeds for the plants in contact with the water. The water may be substantially stationary or may be flowing with respect to the plants. In some embodiments, the step of contacting may include contacting the plants with an industrial and/or municipal effluent.

IV. Examples

The following examples describe selected aspects and embodiments of the present disclosure, such as exemplary methods of making transgenic plants (including algae) and transgenic fungi that metabolize phosphite as a source of phosphorus, exemplary transgenic plants and transgenic fungi, and exemplary methods of using a gene encoding a phosphite dehydrogenase enzyme as a selectable marker for selection of transgenic plants and transgenic fungi. The examples are presented for illustration only and are not intended to define or limit the scope of the present disclosure.

Example 1. Exemplary Generation of Transgenic Plants Expressing a Bacterial Phosphite Dehydrogenase Enzyme This example describes an exemplary method of generating transgenic plants with modified phosphorus metabolism; see FIGS. 4-6.

Figure 4:
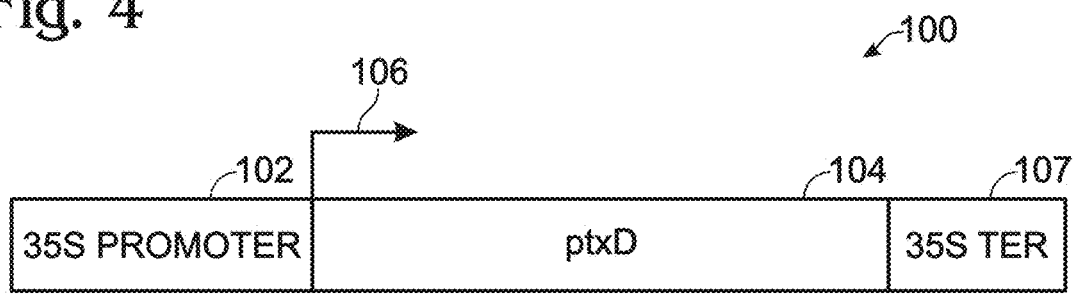
FIG. 4 is a schematic representation of an exemplary chimeric gene constructed for use in generating a transgenic plant that metabolizes phosphite to phosphate, in accordance with aspects of the present disclosure.

FIG. 4 shows an exemplary nucleic acid, a chimeric gene 100, constructed for use in generating a transgenic plant that metabolizes phosphite to phosphate, to permit growth on phosphite in the absence of phosphate. The gene was constructed using the Gateway® system (Gateway® Technology, 2003, Invitrogen) as described in the following paragraphs.

Gene 100 includes a 35S promoter sequence 102 from Cauliflower Mosaic Virus (CaMV) operatively linked to a coding sequence 104 (SEQ ID NO:21) from ptxD of *Pseudomonas stutzeri* WM88. Expression of gene 100, indicated at 106, to produce the PtxD polypeptide (a phosphite dehydrogenase enzyme) is thus controlled/driven by 35S promoter 102. Gene 100 optionally may include a termination sequence 107, such as a 35S terminator from CaMV, disposed downstream of and operatively linked to the coding sequence (and promoter sequence). The gene further may include a 5' untranslated sequence disposed between the promoter sequence and the ptxD coding sequence, and/or a 3' untranslated sequence disposed between the ptxD coding sequence and the termination sequence. Furthermore, the gene may include an intron that is transcribed along with ptxD coding sequence and that is removed from the transcript by post-transcriptional splicing.

FIG. 5 shows a schematic diagram of a portion of a strategy used to create gene 100 of FIG. 4. A forward primer 108 (SEQ ID NO:22) and a reverse primer 110 (SEQ ID NO:23) were synthesized. Each primer has a hybridization region 112, 114 that hybridizes, indicated at 116, 118 in the lower part of the figure, in either a forward or reverse orientation to the ends of ptxD coding region 104. Each primer has an attB site 120, 122 (attB1 or attB2) positioned 5-prime to hybridization region 112 or 114. The primers were utilized to amplify coding sequence 104 from a plasmid (pWM302) using the polymerase chain reaction, to create a ptxD amplified product. A construct of the expected size, about 1000 base pairs, was generated, as detected by gel electrophoresis and staining of the amplified product. The primers alternatively may be designed to amplify additional untranslated sequences from upstream and/or downstream of the ptxD coding sequence.

The ptxD amplified product next was incorporated into a plasmid vector using site-specific recombination provided by the Gateway® system. The amplified product was recombined with plasmid pDONR221, via the attP1 and attP2 sites of pDONR 221 and the attB1 and attB2 sites of the amplified product, to create a ptxD derivative of pDONR221, "initial clone" pDONR221. The initial clone has the full-length ptxD coding sequence opposingly flanked by attL1 and attL2 sites.

The ptxD sequence of the initial clone then was moved into an acceptor vector by further site-specific recombination to produce an expression construct, pB7WG2D-ptxD. The acceptor vector was pB7WG2D.1, which includes, in order around the vector, (1) a 35S promoter, (2) attR1 and attR2 sites disposed downstream of the 35S promoter, (3) a 35S terminator, (4) a "bar" gene (confers phosphinothricin resistance) as a selectable marker in plants, (5) a gene, SmSp$^R$, as a selectable marker in bacteria, particularly *Agrobacterium* (confers spectinomycin (Sp) and streptomycin (Sm) resistance), and (6) an EgfpER gene. Gateway®-system directed recombination formed expression clone (pB7WG2D-ptxD) including gene 100 (see FIG. 4), bar, SmSp$^R$, and EgfpER.

The expression construct was used to transform electrocompetent *Agrobacterium tumefaciens* by electroporation. A transformed *Agrobacterium* clone carrying the expression construct was selected for subculture.

The transformed *Agrobacterium* clone was used to transform *Arabidopsis thaliana* (ecotype Col-0) (generally described herein as "wild-type" (WT)) using a modified floral dip method. Transformed T0 progeny were selected using phosphinothricin resistance. In particular, screening was performed with MS 0.1× media containing phosphinothricin (20 mg/L). Twenty-eight resistant lines were identified through PCR amplification of the ptxD gene. Each resistant line was analyzed via T1 progeny using MS 0.1× media containing phosphinothricin (20 mg/L) to look for 3:1 (resistant:sensitive) segregation of the T1 progeny, to identify plants that showed Mendelian transmission of the ptxD gene. Ten homozygous ptxD transgenic plants were established from T2 progeny of T1 progeny exhibiting 3:1 transmission.

The ptxD transgenic plants were tested for their ability to grow in media containing only phosphite (e.g., about 0.1 to 5 mM) as an external source of phosphorus. Control plants showed no substantial growth in this media (i.e., showed growth limited to the internal phosphorus reserves accumulated in the seed), whereas the transgenic plants grew efficiently, thereby demonstrating that the transgenic plants are able to metabolize a reduced form of phosphorus (phosphite) as a source of phosphorus.

Figure 6:
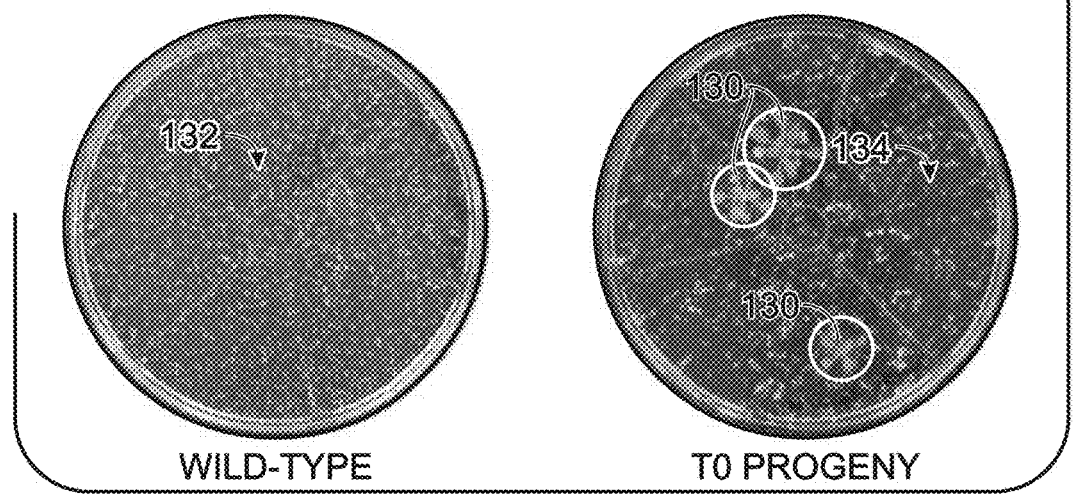
FIG. 6 is a pair of photographs showing exemplary data obtained with the chimeric gene of FIG. 4 used as a selectable marker by selection of transgenic plants for their ability to grow on a phosphite-containing medium in the absence of phosphate, in accordance with aspects of the present disclosure.

The ptxD expression construct also was used to provide a selectable marker for selection of transgenic plants with modified phosphorus metabolism. Wild-type Col-0 plants were transformed using *Agrobacterium* containing the ptxD expression construct. T0 progeny (seeds) were plated on a medium with phosphite (5 mM) as the source of phosphorus. FIG. 6 shows exemplary data for growth of the T0 progeny, relative to wild type plants, on the phosphite medium. Transgenic plants 130 (circled in the right panel) have a substantial growth advantage relative to wild type plants 132 (left panel) and relative to other T0 progeny 134 that apparently were not transformed with the expression construct and/or that did not efficiently express the PtxD polypeptide from the introduced construct.

Further aspects of generating transgenic plants with modified phosphorus metabolism are described in U.S. Provisional Patent Application Ser. No. 61/199,784, filed Nov. 19, 2008, which is incorporated herein by reference.

Example 2. Characterization of *Arabidopsis* Plants Expressing PtxD

This example presents an investigation of the growth characteristics of the parental ("wild-type" (WT) or control) *Arabidopsis* line, Col-0, and two of the transgenic *Arabidopsis* lines described in Example 1 and comprising the ptxD expression construct of Example 1; see FIGS. 7-12.

Two transgenic *Arabidopsis* lines, dubbed PTXD-3 and PTXD-5, were prepared and isolated as described in Example 1. Each line is homozygous for the ptxD expression construct of Example 1.

The parental line and the PTXD-3 and PTXD-5 transgenic lines were tested for the ability to grow on a liquid medium, with or without inorganic phosphate (Pi) as the source of phosphorus. Seeds from the parental and transgenic lines were germinated in liquid media and tested for growth. In the absence of phosphate (and phosphite), neither the parental line nor the transgenic lines showed significant growth beyond germination. (Each line exhibited paltry growth for a short time, which apparently was permitted by phosphate stores in the seeds, which are quickly depleted from the seeds.) In contrast, both the parental (WT) line and the transgenic lines grew efficiently in the presence of 50, 100, and 1000 μM phosphate.

Figure 7:
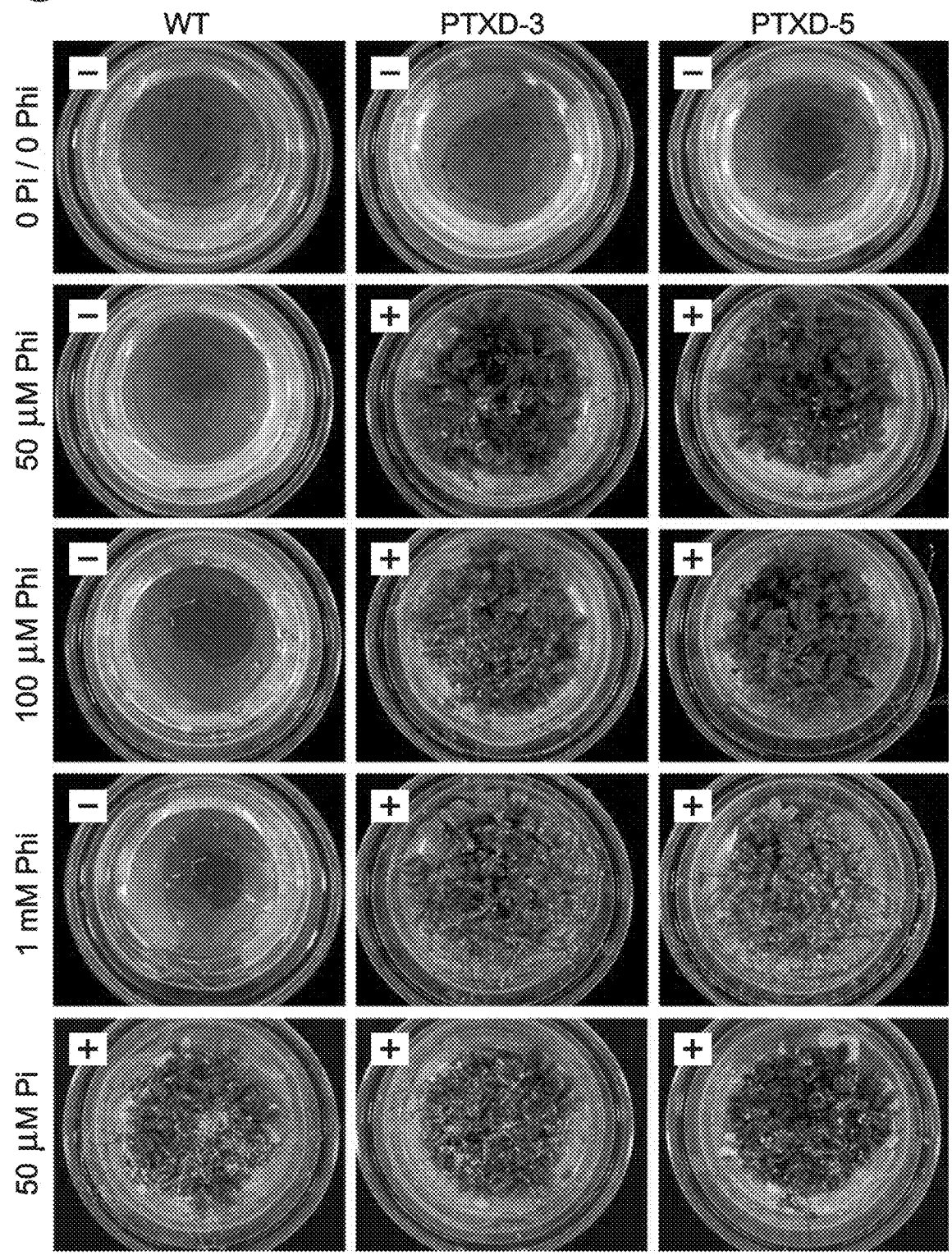
FIG. 7 is a series of photographs of data obtained from growth tests of control and transgenic (ptxD) *Arabidopsis* lines germinated and cultivated in a liquid growth medium, with or without phosphite (Phi) or phosphate (Pi) as the source of phosphorus, in accordance with aspects of the present disclosure.

FIG. 7 shows photographs of data obtained from tests of the growth of the parental (WT) line and the transgenic PTXD-3 and PTXD-5 lines on a liquid growth medium, with or without phosphite (Phi) or phosphate (Pi) as the source of phosphorus. In FIG. 7, the absence or presence of sustained plant growth (beyond the germination stage) is identified with a minus (−) or a plus (+) symbol, respectively. Both the parental line and the transgenic lines grew efficiently in the presence of 50 μM inorganic phosphate (bottom row). Also, neither the parental line nor the transgenic lines showed detectable growth in the absence of both phosphate and phosphite. However, both transgenic lines, but not the parental line, grew efficiently in the presence of 50, 100, and 1000 μM inorganic phosphite as phosphorus source. Therefore, the transgenic lines acquired the ability to metabolize phosphite as a phosphorus source to support plant growth.

Figure 8:
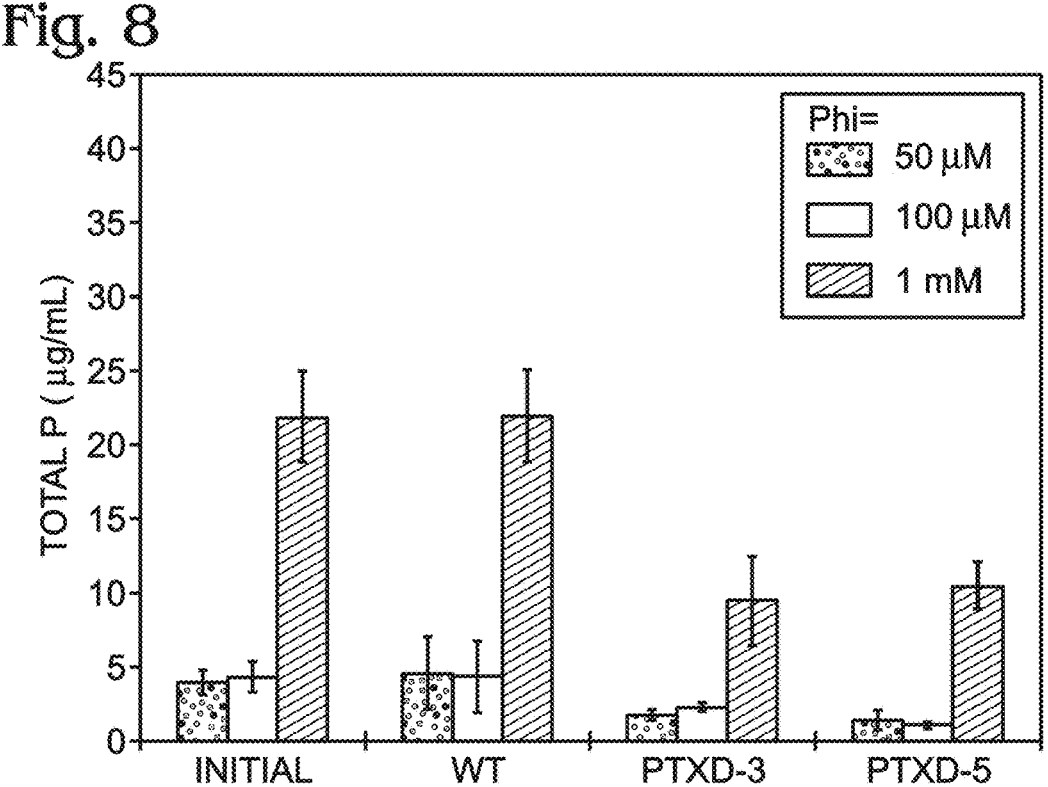
FIG. 8 is a bar graph of data obtained from tests of the ability of the *Arabidopsis* lines of FIG. 7 to extract phosphorus from their growth media, with the plants cultivated for 45 days in growth media containing different concentrations of phosphite (Phi) as the source of phosphorus, in accordance with aspects of the present disclosure.

FIG. 8 shows a bar graph of data obtained from tests of the ability of the wild-type and transgenic *Arabidopsis* lines of FIG. 7 to reduce the amount of total phosphorus in a growth medium containing different concentrations of phosphite (50, 100, and 1000 μM) as the source of phosphorus.

Wild type and the two transgenic *Arabidopsis* lines, PTXD-3 and PTXD-5, were germinated and cultivated in one-liter plastic containers with 0.1× Murashige and Skoog liquid medium lacking phosphate and supplemented with either 50, 100 or 1000 micromolar phosphorous acid ($H_3PO_3$). One hundred plants per plastic container were allowed to grow for 45 days in the plastic container in a growth chamber with a 16:8 light:dark cycle for each 24-hour period. The plants were covered to avoid moisture loss. A double layer of plastic mesh was placed where seeds were sown to germinate on top of liquid media in each plastic container.

After 45 days of growth the total phosphorus content was determined in the liquid media, after removing the plants, using a vanadium-molybdate method. Briefly, 5 mL of liquid media from each sample was digested with nitric acid: perchloric acid ($HNO_3$:$HClO_4$; 5:1). Then, the phosphorus content was determined with a colorimetric method based on the addition of a solution of ammonium molybdate (20 mM) and ammonium metavanadate (10 mM) in 70% perchloric acid. After a 20-minute incubation at room temperature, the absorbance at 400 nm was measured with a spectrophotometer.

In FIG. 8, the first three bars labeled as "initial" represent the initial concentration of total phosphorus in the media without plants. The sets of bars labeled as WT (Col-0), PTXD-3, and PTXD-5 represent the total phosphorus content in the media (initially 50 μM, 100 μM, or 1000 μM phosphite) after 45 days of incubation in the presence of the corresponding *Arabidopsis* lines. The transgenic plants (PTXD-3 and PTXD-5), but not the wild-type plants, diminished the phosphorus content in the media by more than 50%. The decrease in phosphorus content, which in this case represents a removal of phosphite from the media, is due to the uptake of phosphite by the plants. The transgenic lines have a high capacity to remove phosphite from the media because they are able to convert it into phosphate, which sustains plant growth. This ability to remove phosphite from an aqueous medium may be exploited to remove phosphite from waste water, such as effluents produced by CD/DVD factories.

Figure 9:
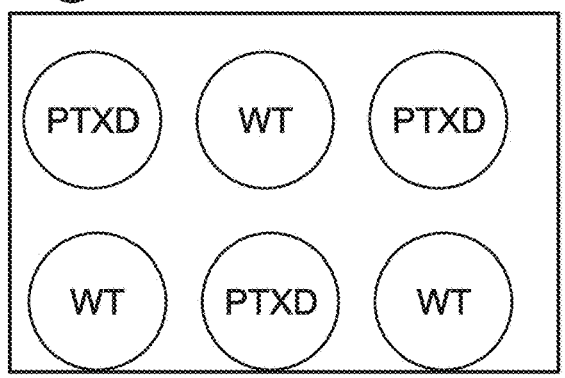
FIG. 9 is a schematic representation of the distribution of control (WT) and ptxD transgenic (PTXD) *Arabidopsis* plants across a growth substrate, as used for the experiments of FIGS. 10 and 11, in accordance with aspects of the present disclosure.
Figure 10:
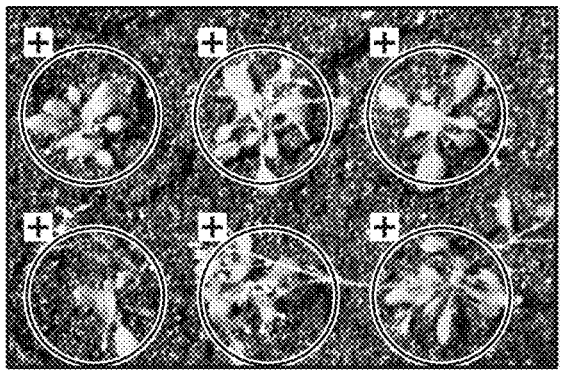
FIG. 10 is a photograph of parental and ptxD transgenic plants distributed according to FIG. 9 and tested for growth on a substrate containing phosphate (Pi) as the source of phosphorus, in accordance with aspects of the present disclosure.
Figure 11:
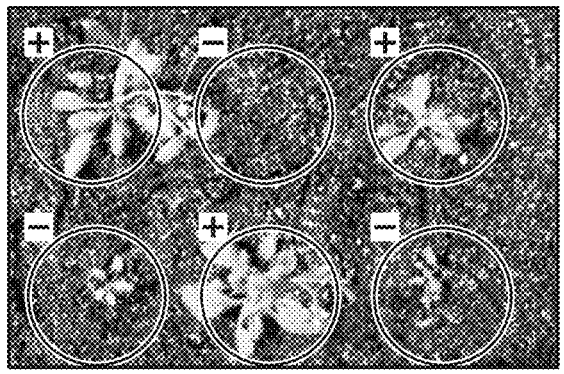
FIG. 11 is a photograph of parental and ptxD transgenic plants distributed according to FIG. 9 and tested for growth on a substrate containing phosphite (Phi) as the source of phosphorus, in accordance with aspects of the present disclosure.

FIG. 9 shows a schematic representation of the distribution of parental (WT) and ptxD transgenic (PTXD) *Arabidopsis* plants used for the experiments of FIGS. 10 and 11.

FIGS. 10 and 11 show photographs of parental and ptxD transgenic plants distributed according to FIG. 9 and tested for growth on a substrate containing added phosphate (Pi) (FIG. 10) or phosphite (Phi) (FIG. 11) as the source of phosphorus. The presence or absence of sustained growth (beyond the germination stage) is indicated by a plus (+) or a minus (−) symbol, respectively. FIG. 10 shows similar growth of wild-type and transgenic plants on phosphate. In contrast, FIG. 11 shows that only the transgenic plants were capable of sustained growth on phosphite. The plants here and in FIG. 11 were grown in a sand:vermiculite mixture (1:1) and received water and nutrient solutions (lacking any other phosphorus source except as previously indicated) periodically.

Figure 12:
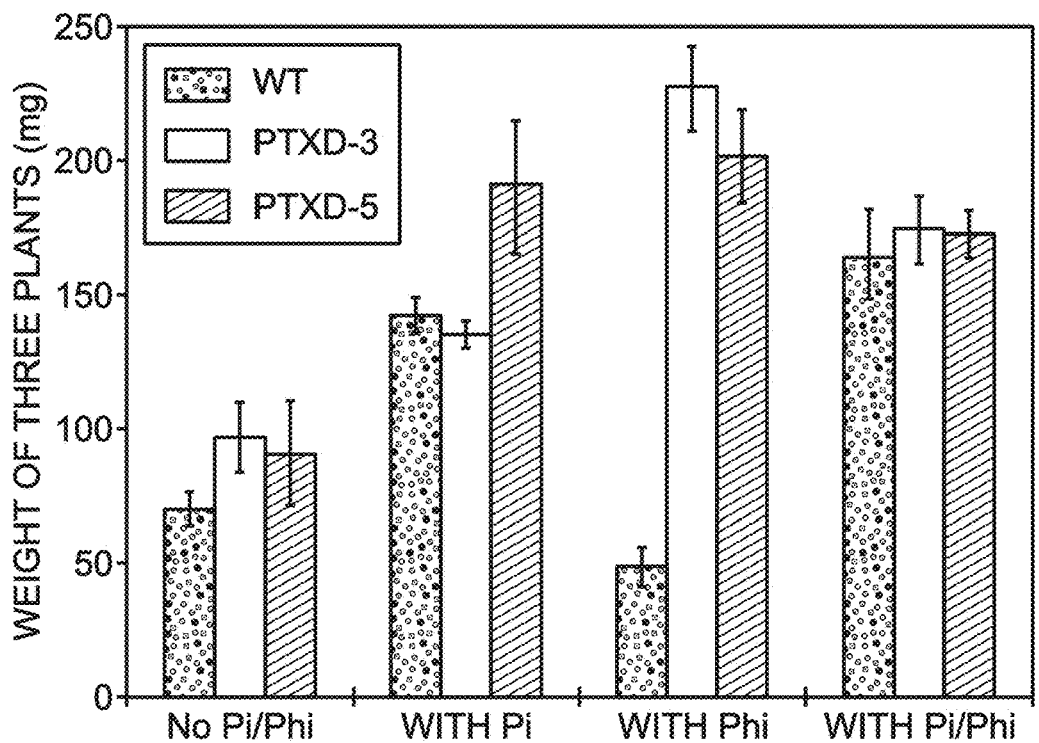
FIG. 12 is a bar graph of data obtained from tests of the ability of the *Arabidopsis* lines of FIG. 7 to increase in weight when cultivated in the absence or presence of phosphate and/or phosphite as the source of phosphorus, in accordance with aspects of the present disclosure.

FIG. 12 shows a bar graph of data obtained from tests of the ability of the *Arabidopsis* plant lines of FIG. 7 to increase in weight when cultivated in the presence of various sources of phosphorus. The dry weight of three plants cultivated in sand:vermiculite (1:1) as substrate is plotted in the figure with respect to each particular plant line and source(s) of phosphorus. Wild type plants did not grow substantially with phosphite as the source of phosphorus, while the transgenic lines grew similarly or better on phosphite (Phi) relative to phosphate (Pi).

Example 3. Transgenic Tobacco Plants Expressing PtxD

Figure 13:
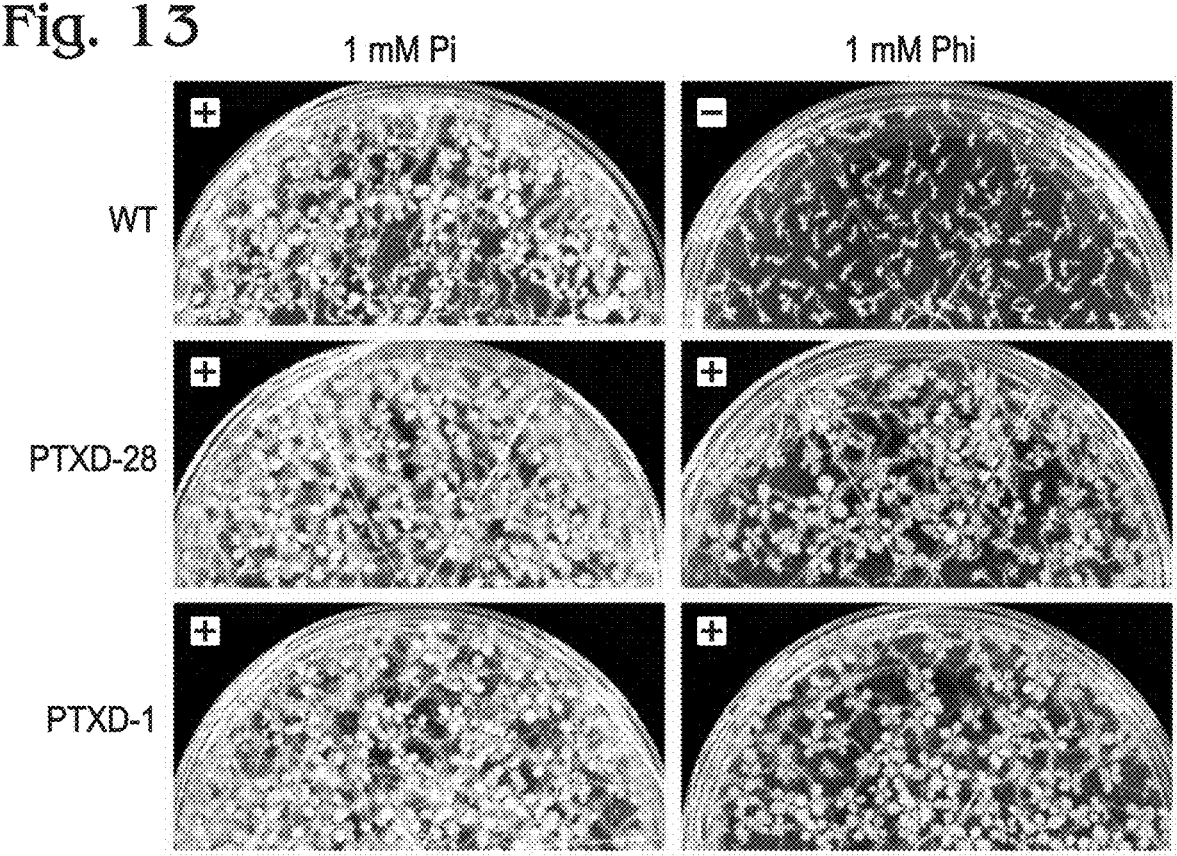
FIG. 13 is a set of photographs of control (WT) and ptxD transgenic lines of *Nicotiana tabacum* (tobacco) 25 days after germination in the presence of phosphate or phosphite as the source of phosphorus, in accordance with aspects of the present disclosure.

This example describes the creation and characterization of transgenic *Nicotiana tabacum* (tobacco) comprising the ptxD expression construct of Example 1; see FIG. 13.

*Nicotiana tabacum* was transformed with the expression construct described in Example 1. In particular, tobacco leaf explants were co-cultivated with an *Agrobacterium* strain harboring a 35S::PtxD construct (Example 1) within its T-DNA. Leaf discs were allowed to regenerate in MS media containing 1 mM phosphite as the only phosphorus source. Plants regenerated from these leaf discs on phosphite-containing media were transferred to soil and allowed to set seed under greenhouse conditions.

FIG. 13 shows photographs of T2 transgenic tobacco seeds, homozygous for the 35S::PtxD gene, and control tobacco seedlings taken 25 days after germination in MS media containing either phosphate (1 mM Pi) or phosphite (1 mM Phi) as the only phosphorus source. The presence or absence of growth (after depletion of seed-furnished phosphorus) is indicated by a plus (+) or a minus (−) symbol, respectively. It can be seen that the control seedlings germinated but were unable to sustain normal growth in phosphite-containing media, compared to when phosphate is supplied as a phosphorus source. In contrast, tobacco plants from each transgenic line showed sustained growth in the presence of phosphite or phosphate as the source of phosphorus. These experiments demonstrate the ability to modify phosphorus metabolism in tobacco.

Figure 14:
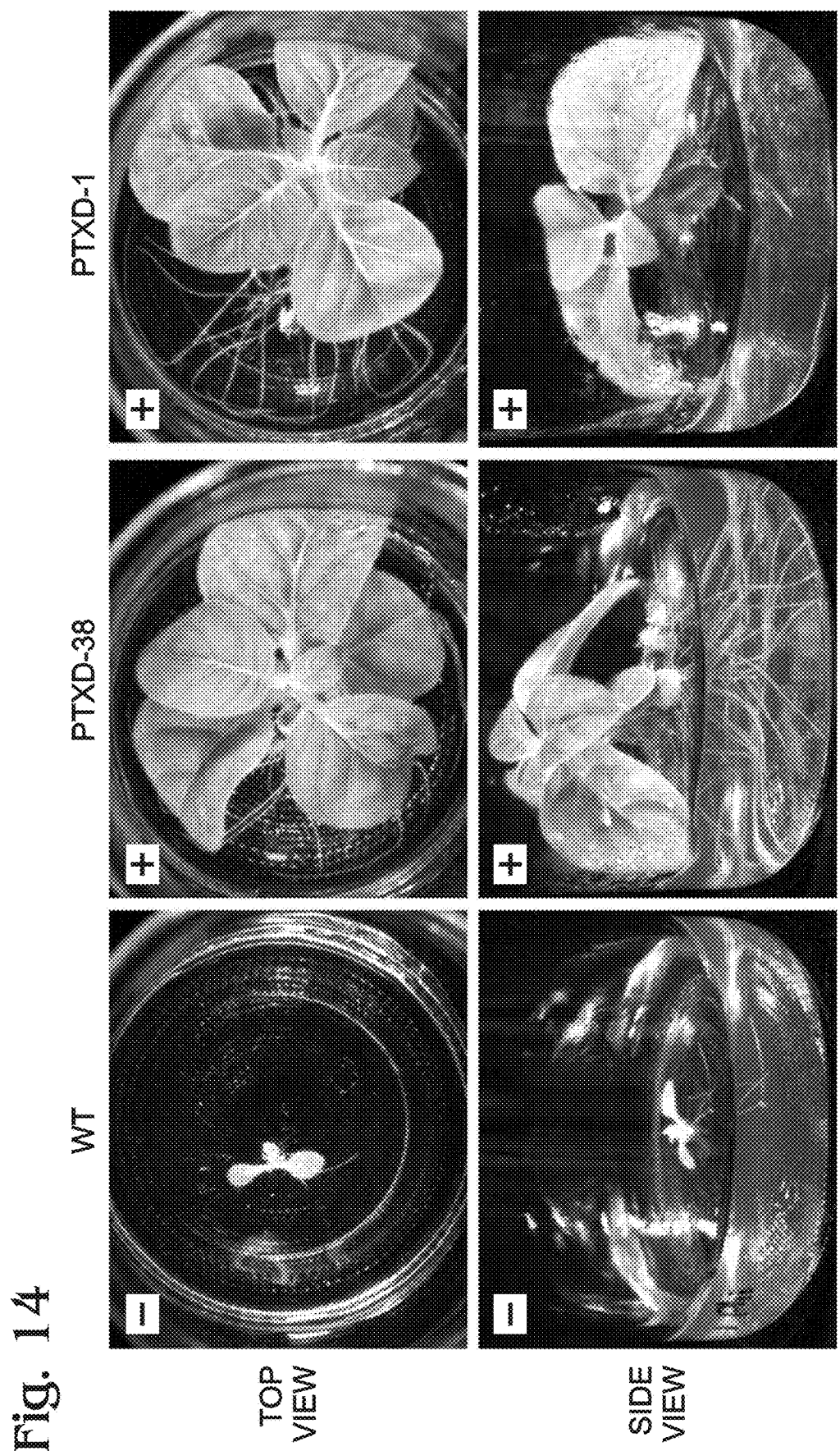
FIG. 14 is a set of photographs of another growth experiment performed with the control and transgenic tobacco lines of FIG. 13, in accordance with aspects of the present disclosure.

FIG. 14 shows photographs of additional growth experiments performed with the control and transgenic tobacco lines of FIG. 13. Seedlings were germinated and maintained in MS media supplemented with 1 mM phosphite as the only phosphorus source for 25 days. The seedlings then were transferred to tissue culture flasks containing MS with 1 mM phosphite as the only phosphorus source and were allowed to grow for 25 additional days in a plant growth chamber at 23° C., with a photoperiod of 18 h light, followed by 6 h darkness for each 24-hour period. It can be observed that the PTXD transgenic plants are able to sustain rapid growth in media containing phosphite as the only phosphorus source, whereas the control plant is unable to use phosphite for its growth and development.

Example 4. Transgenic Algae with Modified Phosphorus Metabolism

This example describes a method of creating a transgenic line of algae expressing a phosphite dehydrogenase enzyme that enables growth of the algae on phosphite as a source of phosphorus.

Photosynthetic algae have been adapted transgenically for many applications, such as production of biofuels, pharmaceuticals, antigens, and the like. The algae can be cultured in large fermentation tanks that incorporate a light system to support photosynthesis and promote growth. Generally, the fermentation tanks must be protected from contamination with undesirable algae (or other organisms). Toward this end, the algae are grown under artificial light rather than sunlight, to reduce the risk of contamination. Accordingly, growth of the algae with exposure to sunlight in open tanks or fields (e.g., in ponds), which would be much cheaper, is not feasible currently because of the high risk of contamination.

The present disclosure enables the use of sunlight and open fields for growth of target algae by modifying the target algae for growth on phosphite as a source of phosphorus. The modified target algae would be capable of thriving in a medium containing phosphite and lacking phosphate, which would not support growth of unwanted (contaminant) algae because they would require phosphate. Accordingly, contamination by the unwanted algae would be reduced or eliminated, permitting the target algae to be cultured at a lower cost in an open tank or field with photosynthesis driven by sunlight.

An expression construct for transformation of an algae species, such as *Chlamydomonas reinhardtii*, is generated. The construct can express any suitable phosphite dehydrogenase (and, optionally, a hypophosphite dehydrogenase, too). In the present illustration, the construct expresses PtxD from the ptxD coding sequence. The construct utilizes a hybrid promoter sequence to drive expression while avoiding gene silencing: the HSP70A promoter is fused upstream of the RBCS2 promoter (each promoter is provided by *C. reinhardtii*) (Schroda et al, 2000, Plant J. 21: 121-131). The hybrid promoter sequence drives expression of the first intron of RBS2 of *C. reinhardtii*, which is fused to the coding sequence of the ptxD gene (*Pseudomonas stutzeri*), which, in turn, is fused to the transcription termination sequence of the RBS2 gene. To enhance expression of PtxD polypeptide from the construct, the ptxD coding sequence may be modified to have a G or C in the third position of codons that permit this change (via degeneracy of the genetic code), to optimize codon usage for translation in *C. reinhardtii*.

The ptxD expression construct may be provided as a plasmid containing an origin of replication functional in *E. coli*, a selectable marker for *E. coli* (e.g., an ampicillin-resistance gene), and a selectable marker functional in *C. reinhardtii*, among others. An exemplary selectable marker for *C. reinhardtii* encodes a zeomycin binding protein that confers resistance to zeomycin and phleomycin (Lumbreras et al., 1998, Plant J. 14: 441-447).

The ptxD expression construct is introduced into *C. reinhardtii* by any suitable mechanism, such as particle bombardment (Debuchy et al., 1989, EMBO J. 8: 2803-2809) or with the aid of glass beads (Kindle et al., 1991, PNAS 88: 1721-1725), among others.

Transformation of C. reinhardtii with glass beads can be carried out as described by Kindle (1990, PNAS 87: 1228-1232). Cell walls are removed from C. reinhardtii cells by incubating them in undiluted autolysin for 30-60 min at room temperature. The effectiveness of treatment is monitored by sensitivity to 0.004% Nonidet P-40 detergent (Sigma). Cells are harvested from autolysin by centrifugation, resuspended in liquid medium, and transformed immediately to avoid cell-wall regeneration. Glass beads (0.45-0.52 mm) are washed with concentrated sulfuric acid, then rinsed thoroughly with distilled water, dried, and sterilized by baking at 250° C. for 2-3 h. Glass beads (300 mg) are added to 0.4 mL of cells, 2 micrograms of plasmid DNA is added, and cells agitated at top speed on a Fisher Vortex Genie II mixer in 15-mL conical disposable polypropylene centrifuge tubes. The beads are allowed to settle, and cells are spread on selective agar plates with a glass spreader. For direct selection of zeomycin-resistant transformants, cells are agitated with glass beads and DNA, diluted in 20 mL TAP liquid medium and left to express the ble gene by incubating at 25° C. in the light (80 µE m$^{-2}$ s$^{-1}$) for 15-18 h with gentle shaking. Cells are then pelleted by centrifugation, resuspended in 5 mL of TAP containing 0.5% molten agar, and poured onto the surface of a TAP/2% agar plate containing zeomycin at 20 mg/m L.

Zeomycin-resistant colonies are then spread in TAP media lacking any source of phosphate, but supplemented with 1 mM phosphite as a phosphorus source. Plates are incubated for 18 to 24 h at 25° C. in light and colonies that grow are able to use phosphite as a phosphorus source.

Example 5. Transgenic Trichoderma Expressing a Phosphite Dehydrogenase

This example describes a method of creating a fungus of the genus Trichoderma modified to express a phosphite dehydrogenase enzyme, to render the fungus capable of growing on phosphite as a source of phosphorus.

A. Introduction

Trichoderma species are free-living fungi that are common in soil and root ecosystems. Recent discoveries show that they behave as avirulent plant symbionts, as well as being parasites of phytophatogenic fungi. Some strains establish robust and long-lasting colonization of root surfaces and penetrate into the epidermis. As ubiquitous soil inhabitants and rhizosphere-competent fungi, Trichoderma species have been used successfully as biological control agents for the management of plant pathogens. Several mechanisms of biocontrol have been proposed for Trichoderma, including competition, mycoparasitism, and the induction of plant defense responses due to colonization of plant root intercellular spaces (Howell, 2003; Yedidia et al., 1999). Root colonization by Trichoderma species also frequently enhances root growth and development, crop productivity, resistance to abiotic stresses, and the uptake and use of nutrients.

Trichoderma species may be modified to express PtxD or an ortholog or derivative thereof, to render the Trichoderma capable of growth on phosphite. Optionally, the Trichoderma also may be modified to express a hypophosphite dehydrogenase (e.g., HtxA). In any event, these transgenic Trichoderma may be put to various uses. For example, they may be used for bioremediation purposes, such as to eliminate phosphite (and/or hypophosphite) from waste water discharge of the CD and DVD industry. The transgenic Trichoderma can be utilized for bioremediation alone, or in combination with a transgenic plant (e.g., Example 1). Use of a combined transgenic plant/fungal system for removal of phosphite (and/or hypophosphite) may be more efficient than the use of either alone. Alternatively, the transgenic Trichoderma can be associated with plants to protect them from pathogen fungi. In this case, the plants may be non-transgenic such that they require phosphate as a source of phosphorus, or may be transgenic plants that can grow on phosphite as a source of phosphorus (e.g., Example 1). In any event, the transgenic Trichoderma may function as a powerful fungicide, since both the Trichoderma itself, and its utilization of phosphite may protect the plants.

B. Protocol

Transformation of Trichoderma atroviride (IMI 206040) protoplasts is carried out using methods known to the art, such as the PEG-CaCl$_2$) method (Herrera-Estrella et al., 1990; Baek & Kenerley, 1998), biolistics (Lorito et al., 1993), or electroporation (Goldman et al., 1990), among others. The transforming DNA is a plasmid or a PCR product carrying a gene encoding a phosphite dehydrogenase enzyme (e.g., PtxD) under control of the Trichoderma reesei pki promoter or the Aspergillus nidulans trpC promoter, and the T. atroviride blu17 or the A. nidulans trpC terminator. Plasmids are purified using the Qiagen Plasmid Midi Kit or cesium chloride gradients. For selection, 100, 200, and 500 µL aliquots are plated using an agar overlay containing 1.2 M sorbitol and 200 mM H$_3$PO$_3$ as sole phosphorus source, immediately after treatment or after a 2-4 hour incubation period of the protoplasts in 1.2 M sorbitol. After three to four days of incubation at 28° C., colonies capable of growth on phosphite as the phosphorus source should appear on the plates. Transformants should appear only when transformed with constructs carrying the ptxD coding sequences. Transformants are subjected to three rounds of monosporic culture to obtain homokaryons. Alternatively, Trichoderma transformants may be obtained by co-transformation using an antibiotic resistance marker for selection (such as hph, which confers hygromycin resistance), in combination with a construct carrying the ptxD gene. Under the latter strategy, hygromycin-resistant transformants carrying the ptxD gene are first selected, and strains capable of using phosphite as a phosphorus source can be selected at a later stage as mentioned above, or are identified in a screen by testing expression of the ptxD gene.

Conidia of transformants carrying a phosphite-utilization cassette are produced by solid or submerged fermentation processes known in the art (Cavalcante et al., 2008). The conidia may be applied to plants, seeds therefor, or to soil, among others. For example, the conidia may be applied to seeds (e.g., with a latex sticker, such as Rhoplex B-15J), directly to plant roots as a spore suspension (e.g., with a sticker), or to soil in water as a spore suspension or in a wheat bran/peat preparation mixture (0.5%, w/w), among others.

The following references are incorporated herein by reference:

Baek, J. M. & Kenerley, C. M. (1998). The arg2 gene of Trichoderma virens: cloning and development of a homologous transformation system. Fungal Genet. Biol. 23:34-44.

Cavalcante, R. S., Lima, H. L. S., Pinto, G. A. S., Gava, C. A. T., and Rodrigues, S. (2008). Effect of Moisture on Trichoderma Conidia Production on Corn and Wheat Bran by Solid State Fermentation. Food Bioprocess. Technol. 1:100-104.

Goldman, G. H., Van Montagu, M., and Herrera-Estrella, A. (1990). Transformation of *Trichoderma harzianum* by high-voltage electric pulse. Curr. Genet. 17:169-174.

Herrera-Estrella, A., Goldman, G. H., and Van Montagu, M. (1990). High efficiency transformation system for the biocontrol agents, *Trichoderma* spp. Mol. Microbiol. 4:839-843.

Howell, C. R. (2003) Mechanisms employed by *Trichoderma* species in the biological control of plant diseases. Plant Dis. 87:4-10.

Lorito, M., Hayes, C. K., Di Pietro, A., and Harman, G. E. (1993). Biolistic transformation of *Trichoderma harzianum* and *Gliocladium virens* using plasmid and genomic DNA. Curr. Genet. 24:349-356.

Yedidia, I., Benhamou, N., and Chet, I. (1999). Induction of defense responses in cucumber plants (*Cucumis sativus* L.) by the biocontrol agent *Trichoderma harzianum*. Appl. Environ. Microbiol. 65:1061-1070.

Example 6. Mycorrhizae Formed with a Fungus Expressing a Bacterial Phosphite Dehydrogenase Enzyme This example describes a method of creating a mycorrhizal-type fungus modified transgenically to express a phosphite dehydrogenase enzyme (and/or a bacterial hypophosphite dehydrogenase enzyme), which renders the transgenic fungus capable of growing on phosphite (and/or hypophosphite) as the source of phosphorus. A method is also disclosed of forming mycorrhizae by associating the transgenic fungus with a plant. Mycorrhizae formed with these transgenic fungi and the plant can supply the plant with phosphate for growth. Accordingly, the plant itself would not need to be transgenic, since the mycorrhizae would do all the work of converting phosphite (and/or hypophosphite) into phosphate.

A. Introduction

Phosphorus (P) is an essential nutrient that can limit plant productivity in natural and agricultural ecosystems. A plant can form a natural symbiotic relationship with a mycorrhizal fungus, which acts as an extension of the plant's root system to provide the plant with mineral nutrients, particularly phosphate, in exchange for carbon-containing molecules derived from the plant's photosynthetic activity (Smith and Read, 1997). Mycorrhizal fungi penetrate root cells of the plant, with the plasma membranes of the fungi and plant establishing a close association to form so-called arbuscular structures. Mineral nutrients, particularly phosphate, can be transferred from fungal cells to plant cells in the arbuscular structures. In addition to mineral nutrients, mycorrhizae can also improve the ability of the plant to uptake water and can protect it from heavy metals (Khan, A. G., 2006; Forbes et al., 1998).

Mycorrhizae have to compete with other microorganisms for phosphate availability. Therefore, transgenic mycorrhizal strains that express a gene encoding a phosphite dehydrogenase enzyme capable of converting phosphite into phosphate can be used to supply plants with phosphate. In this case, the mycorrhizal fungus will convert phosphite into phosphate, which then may be transferred to the roots of non-transgenic plants unable to metabolize phosphite. Alternatively, to make the system more efficient, an association of transgenic mycorrhizal fungi and transgenic plants both expressing a gene encoding phosphite dehydrogenase can be used. The association of transgenic mycorrhizal fungi with non-transgenic or transgenic plants can be used to enhance plant productivity using fertilizers in which phosphate has been replaced by phosphite, or to bioremediate effluents from CD or DVD producing factories or soils in which phosphite has been used as a fungicide (Ohtake, H., 1995)

B. Protocol

This example utilizes the ptxD coding sequence from *Pseudomonas stutzeri*. However, any suitable coding sequence for a phosphite dehydrogenase may be exploited.

A gene construct is created by placing the ptxD coding sequence under control of the *Aspergillus nidulans* glyceraldehyde-3-phosphate dehydrogenase (gpd) promoter and the transcription terminator region of the *A. nidulans* tryptophan synthetase (trpC) gene. A selectable marker such as the aph gene from *E. coli*, which confers resistance to hygromycin, or the ble gene, which confers resistance to phleomycin, is also included in the transforming molecule (Barrett et al., 1990).

For transformation, protoplasts of a mycorrhizal fungus (e.g., *Laccaria bicolor, Cenococcum geophilum, Hebeloma cylindrosporium, Paxillus involotus, Gigaspora rosea, Glomus mosseae, Glomus aggregatum, Glomus intraradices, Pisolithus tinctorius*, etc.) are obtained according to the protocol of Barrett et al. (1990). To isolate protoplasts, mycelia are collected and washed several times with sterile water and then treated with hydrolytic enzymes (a mixture of cellulase, chitinase, and proteases, with 5 to 10 mg/mL of each enzyme) in an osmotic solution (PDB; potato-dextrose-broth with 0.8 M mannitol or 0.6 M sucrose) to degrade the cell walls. The mycelia are incubated with the enzymes for 1 to 3 hours at 32° C. with constant agitation (100 rpm). The protoplast suspension is filtered and washed with the osmotic solution. Protoplasts are recovered by centrifugation for 10 min at 800 rpm and the protoplast pellet resuspended in PDB buffer and the number of protoplasts determined by counting under a microscope.

Protoplasts ($1-3 \times 10^7$ in 250 µL) are mixed with 5 to 20 micrograms of the gene construct and incubated in PEG transformation solution (25-60% polyethylene glycol 4000, 10-25 mM $CaCl_2$), 10 mM Tris-HCl, pH 7.5) for 45 minutes at 4° C. One mL of additional PEG transformation solution is added and incubation is continued at room temperature for 20 minutes. Protoplasts are allowed to regenerate cell walls in liquid media and transformants are selected in solid media. The solid media (Potato dextrose agar) contains 100 µg/mL hygromycin or 100 µg/mL of phleomycin, depending on the selectable marker used for the transformation. Growing colonies are transferred to solid media three times to isolate stably transformed mycelia. The presence of the selectable marker as well as the ptxD gene is confirmed by PCR. Once stable transformants are isolated, a 2 mm portion of mycelium is transferred to PDA media lacking phosphate and supplemented with 1 mM phosphite to identify colonies that express the ptxD gene construct. Southern blot analysis is used to confirm the presence of the corresponding genes.

To confirm that the transgenic fungus can provide phosphate to plants, soil is inoculated with mycelia of the ptxD-transformed fungus, and tobacco seed is germinated in the soil. The soil is fertilized with a normal concentration of nitrogen and potassium, with phosphite as the phosphorus source. Growth of tobacco plants from the seed in soil inoculated with the ptxD transgenic fungus is compared to growth in control soil that has not been inoculated.

The following references are incorporated herein by reference:

Barrett, V., Dixon, R. K., and Lemke, P. A. (1990) Genetic transformation of a mycorrhizal fungus. Appl. Micobiol. Biotechnol. 33:313-316.

Bills, S. N., Richter, D. L., and Podila G. K. (1995) Genetic transformation of the ectomycorrhizal fungus *Paxillus involutus* by particle bombardment. Mycological Research 99:557-561.

Bills, S. N., Podila, G. K., and Hiremath, S. T. (1999) Genetic engineering of the ectomycorrhizal fungus *Laccaria bicolor* for use as a biological control agent. Mycologia 91: 237-242.

Forbes, P. J., Millam, S., Hooker, J. E., and Harrier L. A. (1998) Transformation of the arbuscular mycorrhiza *Gigaspora rosea* by particle bombardment. Mycol. Res., 102:497-501.

Hanif, M., Pardo, A. G., Gorier, M., and Raudaskoski, M. (2002) T-DNA transfer and integration in the ectomycorrhizal fungus *Suillus bovinus* using hygromycin B as a selectable marker. Curr. Genet. 41:183-188.

Kemppainen, M., Circosta, A., Tagu, D., Martin, F., and Pardo, A. G. (2005) *Agrobacterium*-mediated transformation of the ectomycorrhizal symbiont *Laccaria laccata* S238N. Mycorrhiza. 16:19-22.

Khan, A. G. (2006) Mycorrhizoremediation—an enhanced form of phytoremediation. Journal of Zhejiang University Science B. 7:503-514.

Marmeisse, R., Gay, G., Debaud, J-C., and Casselton, A. (1992) Genetic transformation of the symbiotic basidiomycete fungus *Hebeloma cylindrosporum*. Curr. Genet., 22:41-45.

Ohtake, H., 1995. Applications of biotechnology to pollution prevention. Bioremediation: the Tokyo '94 Workshop, OECD, Paris, pp. 409-417.

Pardo, A., Hanif, M., Raudaskoski, M., and Gorfer, M. (2002) Genetic transformation of ectomycorrhizal fungi mediated by *Agrobacterium tumefaciens*. Mycol. Res. 106: 132-137.

Pardo, A. G., Kemppainen, M., Valdemoros, D., Duplessis, S., Martin, F., and Tagu, D. (2005) T-DNA transfer from *Agrobacterium tumefaciens* to the ectomycorrhizal fungus *Pisolithus microcarpus*. Revista Argentina de Microbiologia. 37:69-72.

Peng, M, Lemke, P. A., and Shaw J. J. (1993) Improved conditions for protoplast formation and transformation of *Pleurotus ostreatus*. Appl. Micobiol. Biotechnol. 40:101-106.

Smith S. E., and Read D. J. (1997) Mycorrhizal Symbiosis. Academia Press, San Diego, CA USA.

Example 7. Selected References

This example presents a set of references pertinent to aspects of the present disclosure. Each of the references is incorporated herein by reference for all purposes.

A. General Aspects of Phosphite in Plants

Ticconi, C. A., Delatorre, C. A., and Abel, S. (2001) Attenuation of phosphate starvation responses by phosphite in *Arabidopsis*. Plant Physiol. 127:963-972.

Varadarajan, D. K., Karthikeyan, A. S., Matilda, P. D., and Raghothama, K. G. (2002) Phosphite, an analogue of phosphate, suppresses the coordinated expression of genes under phosphate starvation. Plant Physiol. 129: 1232-1240.

Ouimette, D. G., and Coffey, M. D. (1989) Phosphonate levels in Avocado (*Persea amercana*) seedlings and soil following treatment with Fosetyl-Al or potassium phosphonate. Plant Dis. 73:212-215.

Ouimette, D. G., and Coffey, M. D. (1990) Symplastic entry and phloem translocation of phosphonate. Pestic. Biochem. Physiol. 38:18-25.

Niere, J. O., DeAngelis, G., and Grant, B. R. (1994) The effect of phosphonate on the acid-soluble phosphorus components in the genus *Phytophthora*. Can. J. Microbiol. 140:1661-1670.

Guest, D., and Grant, B. R. (1991) The complex action of phosphonates as antifungal agents. Biol. Rev. 66:159-187.

Förster H., Adaskaveg, J. E., Kim, D. H., and Stanghellini, M. E. (1998) Effect of Phosphite on Tomato and Pepper Plants and on Susceptibility of Pepper to *Phytophthora* Root and Crown Rot in Hydroponic Culture. Plant Dis. 82:1165-1170.

Carswell, C., Grant, B. R., Theodorou, M. E., Harris, J., Niere, J. O., Plaxton, W. C. (1996) The Fungicide Phosphonate Disrupts the Phosphate-Starvation Response in *Brassica nigra* Seedlings. Plant Physiol. 110:105-110.

Sukarno N., Smith, S. E., and Scott, E. S. (1993) The effect of fungicides on vesicular arbuscular mycorrhizal symbiosis: I. The effects on vesicular-arbuscular mycorrhizal fungi and plant growth. New Phytol. 25:139-147.

Ohtake, H. (1995). Applications of biotechnology to pollution prevention. Bioremediation: the Tokyo '94 Workshop, OECD, Paris, pp. 409-417.

Ohtake H., Wu, H., Imazu, K., Anbe, Y., Kato, J., and Kuroda, A. (1996) Bacterial phosphonate degradation, phosphite oxidation and polyphosphate accumulation. Resources, Conservation and Recycling 18: 125-134.

Albrigo, L. G. (1999) Effects of foliar applications of urea or nutriphite on flowering and yields of Valencia orange trees. Proc. Fla. State Hort. Soc. 112:1-4.

Fenn, M, E., and Coffey, M. D. (1984) Studies on the In Vitro and In Vivo Antifungal Activity of Fosetyl-Al and Phosphorous Acid. Phytopathology. Vol. 74, No. 5.

Schroetter, S., Angeles-Wedler, D., Kreuzig, R., and Schnug, E. (2006) Effects of phosphite on phosphorus supply and growth of corn (*Zea mays*). Landbauforschung Völkenrode 3/4 2006 (56):87-99.

Rebollar-Alviter, A. L., Madden, L. V., and Ellis, M. A. (2005) Efficacy of Azoxystrobin, Pyraclostrobin, Potassium Phosphite, and Mafenoxam for Control of Strawberry Leather Rot Caused by *Phytophthora cactorum*. Plant Health Progress.

Wilcoxy, W. (2005) ProPhyt, Alliete, and Phosphorous Acid. The Lake Erie Regional Grape Program.

McDonald, A. E., Grant, B. R., and Plaxton, W. C. Phosphite (Phosphorous Acid): Its Relevance in the Environment and Agriculture and Influence on Plant Phosphate Starvation. J. Plant Nutr. 24:1505-1519.

Niere, J. O., DeAngelis, G., and Grant, B. R. (1994) The effect of phosphonate on the acid-soluble phosphorus components in the genus *Phytophthora*. Microbiol. 140: 1661-1670.

Guest, D., and Grant, B. R. (1991) The complex action of phosphonates as antifungal agents. Biol. Rev. 66:159-187.

B. Identification, Cloning, and Characterization of RP-Oxidoreductases

White, A. K., and Metcalf, W. W. (2007) Microbial Metabolism of Reduced Phosphorus Compounds. Annu. Rev. Microbiol. 61:379-400.

White, A. K., and Metcalf, W. W. (2002) Isolation and Biochemical Characterization of Hypophosphite/2-Oxoglutarate Dioxygenase. A Novel Phosphorus-Oxidizing Enzyme from *Pseudomonas stutzeri* WM88. J. Biol. Chem. 277:38262-38271.

Metcalf, W. W., and Wolfe, R. S. (1998) Molecular Genetic Analysis of Phosphite and Hypophosphite Oxidation by *Pseudomonas stutzeri* WM88. J. Bacteriol. 180:5547-5558.

Garcia-Costas, A. M., White, A. K., and Metcalf, W. W. (2001) Purification and Characterization of a Novel Phosphorus-oxidizing Enzyme from *Pseudomonas stutzeri* WM88. J. Biol. Chem. 276: 17429-17436.

Schink, B., Thiemann, V., Laue, H., and Friedrich, M. W. (2002) *Desulfotignum phosphitoxidans* sp. nov., a new marine sulfate reducer that oxidizes phosphite to phosphate. Arch. Microbiol. (2002) 177:381-391.

C. Transformation of Plants

Martinez-Trujillo, M. et al. (2004) Improving Transformation Efficiency of *Arabidopsis thaliana* by Modifying the Floral Dip Method. Plant Mol. Biol. Reporter. 22: 63-70.

Example 8. Selected Embodiments I

This example describes selected embodiments of the invention, presented as a series of indexed paragraphs.

A. A transgenic plant capable of utilizing at least one reduced form of phosphorus as a phosphorus fertilizer. The transgenic plant of this paragraph may be further characterized as follows: (A1) wherein the plant expresses a bacterial coding sequence encoding an enzyme capable of oxidizing phosphite to phosphate, thereby permitting use of phosphite as a phosphorus fertilizer (and a source of phosphorus); (A2) wherein the bacterial coding sequence of A1 is ptxD from *Pseudomonas stutzeri, Alcaligenes faecalis,* or *Xanthobacter flavus*; (A3) wherein the transgenic plant of A1 or A2 expresses htxA and ptxD coding sequences, thereby permitting use of hypophosphite and/or phosphite as a phosphorus fertilizer; (A4) wherein each or both of the bacterial coding sequences of A3 is from *Pseudomonas stutzeri, Alcaligenes faecalis,* or *Xanthobacter flavus*; (A5) wherein at least one of the bacterial coding sequence(s) of any of A1 through A4 is under control of a constitutive promoter, a leaf-specific promoter, a tissue-specific promoter, a root-specific promoter, a promoter inducible by low phosphate, or the 35S promoter from the Cauliflower Mosaic Virus; or (A6) any combination of A1 through A5.

B. The use of a transgenic plant capable of oxidizing hypophosphite to phosphate, and/or phosphite to phosphate, to eliminate hypophosphite and/or phosphite from an industrial or municipal effluent.

C. The use of one or more bacterial coding sequences that oxidize hypophosphite to phosphate, and/or phosphite to phosphate, as a selectable marker for the production of transgenic plants.

D. The use of recombinant DNA molecules composed of one or more bacterial coding sequences encoding enzymes that oxidize hypophosphite to phosphate, and/or phosphite to phosphate, and a promoter sequence functional in plants as a selectable marker for the production of transgenic plants.

E. A chimeric gene functional in a plant cell, which chimeric gene comprises: (1) a plant-expressible promoter sequence; (2) a terminator signal sequence; and (3) a coding region of a bacterial gene that oxidizes phosphite into phosphate, which coding region: encodes a functional NAD:phosphite oxidoreductase enzyme, and is positioned between such plant-expressible promoter sequence and such terminator signal sequence so as to be expressible, wherein expression of such coding region in a plant cell confers the capacity of using phosphite as a phosphorus source on such plant cell and wherein such capacity to use phosphite as a phosphorus source is capable of providing a basis for selection of such plant cell. The chimeric gene of this paragraph may be further characterized as follows: (E1) wherein the coding region is from the ptxD gene from *Pseudomonas stutzeri, Alcaligenes faecalis,* or *Xanthobacter flavus*; (E2) wherein the promoter sequence is a constitutive promoter; (E3) wherein the promoter sequence is the 35S promoter from Cauliflower Mosaic Virus; (E4) wherein the terminator signal sequence is a nopaline synthetase terminator signal sequence; (E5) wherein the terminator signal sequence is a Cauliflower Mosaic Virus terminator signal sequence; or (E6) any combination of E1 through E5.

F. A transgenic plant that expresses at least one foreign enzyme at a level enabling the plant to metabolize a reduced form of phosphorus as a phosphorus fertilizer.

Example 9. Selected Embodiments II

This example describes selected embodiments of the invention, presented as a series of indexed paragraphs.

A. A transgenic plant comprising a construct that confers (1) a growth advantage on the plant for growth using a reduced form of phosphorus as a nutrient and/or (2) a capability to metabolize at least one reduced form of phosphorus. The transgenic plant of this paragraph may be further described as follows: (A1) wherein the construct confers a growth advantage on the plant if phosphite is an at least substantially exclusive external source of phosphorus for the plant; (A2) wherein the construct confers a growth advantage on the plant if hypophosphite is an at least substantially exclusive external source of phosphorus for the plant; (A3) wherein the construct confers a growth advantage on the plant if phosphite is an at least substantially exclusive external source of phosphorus for the plant and if hypophosphite is an at least substantially exclusive external source of phosphorus for the plant; (A4) wherein the transgenic plant is capable of growth without phosphate as an external source of phosphorus, and wherein a non-transgenic variety of the transgenic plant lacking the construct is at least substantially unable to grow without phosphate as an external source of phosphorus; (A5) wherein the transgenic plant was transformed initially with the construct in a progenitor of the transgenic plant; (A6) wherein the construct encodes expression of one or more polypeptides that confer on the plant a capability to metabolize at least one reduced form of phosphorus to phosphate, and, optionally, wherein at least one of the polypeptides oxidizes phosphite to phosphate, and, optionally, wherein at least one of the polypeptides is capable of using nicotinamide adenine dinucleotide (NAD+) and/or nicotinamide adenine dinucleotide phosphate (NADP+) as an electron acceptor, and, optionally, wherein the one or more polypeptides include a PtxD polypeptide, which, optionally, is encoded by a coding region originating at least substantially from *Pseudomonas stutzeri, Alcaligenes faecalis,* or *Xanthobacter flavus*; (A7) wherein the one or more polypeptides of A6 include an HtxA polypeptide; (A8) wherein expression of at least one of the one or more polypeptides of A6 or A7 is inducible; (A9) wherein expression of at least one of the polypeptides of any of A6 through A8 is inducible by low phosphate; (A10) wherein expression of at least one of the polypeptides of any of A6 through A9 is under control of a constitutive promoter; (A11) wherein expression of at least one of the polypeptides of any of A6 through A10 is under control of a leaf-specific promoter; (A12) wherein expression of at least one of the polypeptides of any of A6 through A11 is under control of a root-specific promoter; (A13) wherein expression of at least one of the polypeptides of any of A6 through A12 is under control of a promoter that is not tissue specific; or (A14) any combination of A1 through A13.

B. A transgenic plant comprising a construct encoding a bacterial polypeptide that confers on the plant a capability to metabolize phosphite to phosphate.

C. A seed that germinates to produce, or any plant part used to produce or vegetatively reproduce, the transgenic plant of paragraph A or B.

D. A nucleic acid for generating a transgenic plant, comprising: a chimeric gene capable of conferring on a plant (1) a growth advantage for growth using a reduced form of phosphorus as a nutrient and/or (2) a capability to metabolize at least one reduced form of phosphorus. The nucleic acid of this paragraph may be further described as follows: (D1) wherein the chimeric gene includes a promoter operatively linked to a coding region, and wherein the promoter is capable of controlling expression of the coding region in a plant, and, optionally, wherein the coding region encodes one or more polypeptides that oxidize phosphite to phosphate, and, optionally, wherein the coding region is provided at least substantially by a ptxD gene; (D2) wherein the chimeric gene includes a promoter operatively linked to a coding region, and wherein the promoter originated at least substantially in a plant and/or a plant virus, and, optionally, wherein the promoter includes a 35S promoter from Cauliflower Mosaic Virus; (D3) further comprising a transcriptional terminator that is functional in a plant and operatively linked to the promoter and the coding region of D1 or D2; (D4) wherein the coding region of any of D1 through D3 encodes a polypeptide that oxidizes phosphite to phosphate; (D5) wherein the nucleic acid is disposed in a microorganism; (D6) wherein the nucleic acid is isolated from cells; (D7) wherein the nucleic acid is disposed in a transgenic plant; or (D8) any combination of D1 through D7.

E. A method of generating a transgenic plant, comprising: selecting for transformation of a plant or plant part using, as a selectable marker, a nucleic acid that confers a capability to metabolize a reduced form of phosphorus. The method of this paragraph may be further described as follows: (E1) wherein the step of selecting for transformation includes a step of selecting for a growth advantage of the plant or plant part, relative to other plants or plant parts, with one or more reduced forms of phosphorus as an external source of phosphorus for the plants or plant parts; (E2) wherein the step of selecting for a growth advantage in E1 is performed with the plants or plant parts in contact with a medium containing phosphite, hypophosphite, or both; (E3) wherein the step of selecting for a growth advantage of E1 or E2 is performed with the medium containing at least substantially no phosphate; (E4), further comprising a step of contacting the plant or plant part, a progenitor thereof, or both, with a modifying agent including a construct that provides the selectable marker; (E5) wherein the modifying agent of E4 includes *Agrobacterium* cells containing the construct; (E6) wherein the construct of E4 or E5 encodes a polypeptide that oxidizes phosphite to phosphate; (E7) wherein the construct of any of E4 through E6 encodes a polypeptide that oxidizes hypophosphite to phosphate; (E8) wherein the step of contacting of any of E4 through E7 includes a step of firing projectiles at the plant or plant part, a progenitor thereof, or both; (E9) wherein the step of selecting for transformation is performed with a plant part, and wherein the plant part is a tissue explant or an isolated plant cell; or (E10) any combination of E1 through E9.

F. A method of fertilizing the transgenic plant of paragraph A or B, wherein a reduced form of phosphorus is used as foliar fertilizer or added to amend soil composition to provide a source of phosphate to sustain plant growth and reproduction.

G. A method of water remediation, comprising: contacting (i) an effluent including phosphite and (ii) a transgenic plant comprising a construct that confers a capability to metabolize phosphite to phosphate, thereby reducing a level of phosphite in the effluent.

Example 10. Selected Embodiments III

This example describes selected embodiments of the invention, presented as a series of indexed paragraphs.

A. A nucleic acid, comprising: a chimeric gene including (a) a coding region that encodes a phosphite dehydrogenase enzyme and (b) a transcription promoter operatively linked to the coding region, wherein the promoter is heterologous with respect to the coding region and is functional in plants, fungi, or both, and wherein the chimeric gene provides sufficient expression of the enzyme, in a plant or fungal cell containing the chimeric gene, to confer an ability on the cell to metabolize phosphite (Phi) as a phosphorus source for supporting growth, thereby enabling growth of the cell without an external source of phosphate (Pi). The nucleic acid of this paragraph may be described further as follows: (A1) wherein the phosphite dehydrogenase enzyme is of bacterial origin; (A2) wherein the phosphite dehydrogenase enzyme is PtxD of *Pseudomonas stutzeri* (SEQ ID NO:1), an analog or derivative of PtxD (SEQ ID NO:1), or a PtxD-like homolog from another bacterial species; (A3) wherein the bacterial phosphite dehydrogenase enzyme has an amino acid sequence with at least 50%, 60%, 80%, 90%, or 95% sequence identity to at least one of SEQ ID NOS:1-14; (A4) wherein the phosphite dehydrogenase enzyme has an amino acid sequence including a first sequence region having an NAD-binding motif with sequence similarity or identity to VGILGMGAIG (SEQ ID NO:15), a second sequence region having sequence similarity or identity to XPGALL-VNPCRGSVVD (SEQ ID NO:16), where X is K or R, a third sequence region having sequence similarity or identity to GWX$_1$PX$_2$X$_3$YX$_4$X$_5$GL (SEQ ID NO. 19), where X$_1$ is R, Q, T, or K, X$_2$ is A, V, Q, R, K, H, or E, X$_3$ is L or F, X$_4$ is G, F, or S, and X$_5$ is T, R, M, L, A, or S, or includes any combination of the first, second, and third sequence regions; (A5) wherein the phosphite dehydrogenase enzyme has an amino acid sequence that is at least 90% identical to PtxD from *Pseudomonas stutzeri* (SEQ ID NO:1); (A6) wherein the chimeric gene further includes a transcription terminator that is operatively linked to the coding region and heterologous with respect to the coding region; (A7) wherein the promoter is a plant promoter or a viral promoter of a plant virus and is capable of promoting the sufficient expression of the enzyme in a plant cell; (A8) wherein the promoter of A7 corresponds to the 35S promoter of Cauliflower Mosaic Virus; (A9) wherein the promoter of A7 is inducible by low phosphate availability; (A10) wherein the promoter of A9 corresponds to a promoter of the PLDZ2 gene of *Arabidopsis thaliana*; (A11) wherein the chimeric gene is capable of promoting the sufficient expression of the enzyme both in a plant cell and in a fungal cell each containing the chimeric gene; (A12) wherein the promoter is a fungal promoter capable of promoting the sufficient expression of the enzyme in a fungal cell; (A13) wherein one or more codons of the coding region have been changed in vitro to improve translational efficiency in plants and/or fungi; (A14) further comprising an intron connected to the coding region and configured to be transcribed with the coding region and removed by splicing after transcription, wherein the intron is optionally disposed within the coding region; (A15) wherein the coding region has at least 90% sequence identity with SEQ ID NO:21; or (A16) any combination of A1 through A15.

B. A plant cell comprising a nucleic acid that expresses a phosphite dehydrogenase enzyme in the plant cell and capable of metabolizing phosphite as a source of phosphorus for supporting growth. Optionally, the nucleic acid is according to paragraph A. The plant cell of this paragraph may be described further as follows: (B1) further comprising an other nucleic acid that expresses a hypophosphite dehydrogenase enzyme, optionally of bacterial origin, in the plant cell; (B2) the plant cell of B1 wherein the nucleic acids collectively confer an ability on the cell to metabolize hypophosphite (Hphi) as a phosphorus source for supporting growth; (B3) wherein the other nucleic acid of B1 or B2 encodes a polypeptide with at least 95% sequence identify to HtxA of *Pseudomonas stutzeri* (SEQ ID NO:20); (B4) the plant cell of any of B1 through B3, wherein the nucleic acids are integrated adjacent one another in the genome of the plant cell; (B5) wherein expression of the phosphite dehydrogenase enzyme, the hypophosphite dehydrogenase enzyme, or both are controlled by a root-specific promoter; (B6) wherein the plant cell is homozygous for the nucleic acid; (B7) wherein the plant cell is a eukaryotic algal cell; (B8) wherein the algal cell of B7 is a *Chlamydomonas* cell; (B9) wherein the plant cell is from a species of vascular plant; or (B10) any combination of B1 through B9.

C. A plant composed of a plurality of plant cells according to paragraph B. The plant of this paragraph may be described further as follows: (C1) wherein the plant is a vascular plant, such as a species of crop plant, (C2) wherein the species of crop plant of C1 is selected from the group consisting of maize, soybean, rice, potatoes, tomatoes, sugarcane, and wheat.

D. A fungal cell comprising a nucleic acid that expresses a phosphite dehydrogenase enzyme in the fungal cell and capable of metabolizing phosphite as a source of phosphorus for supporting growth. Optionally, the nucleic acid is according to paragraph A. The fungal cell of this paragraph may be described further as follows: (D1) further comprising a nucleic acid that expresses a bacterial hypophosphite dehydrogenase enzyme in the fungal cell; (D2) the fungal cell of D1, wherein the nucleic acids collectively confer an ability on the cell to metabolize hypophosphite (Hphi) as a phosphorus source for supporting growth of the fungal cell; (D3) wherein the fungal cell is from a species of *Trichoderma*; (D4) wherein the fungal cell is a member of a species of mycorrhizal fungus capable of forming a symbiotic relationship with a plant; or (D5) any combination of D1 through D4.

E. A method of reducing fungal infections in plants, comprising: applying a plurality of the fungal cells of paragraph D to a seed form of plants, the plants themselves, soil in which the plants are disposed, or a combination thereof. In some cases, the fungal cells may be spores.

F. A plant associated with a plurality of fungal cells according to paragraph D to form mycorrhizae. Optionally, the fungal cells render the plant capable of growing on a medium containing phosphite (Phi), hypophosphite (Hphi), or both, as a phosphorus source for supporting growth.

G. A method of fertilizing a crop plant using hypophosphite and/or phosphite as a phosphorus source for supporting growth, the crop plant (a) including a plurality of cells comprising the nucleic acid of paragraph A, (b) forming mycorrhizae with a mycorrhizal fungus comprising the nucleic acid of paragraph A, and/or (c) being associated with a *Trichoderma* fungus comprising the nucleic of claim 1, the method comprising: applying at least one reduced form of phosphorus to the plant and/or to soil adjacent the plant, such that the reduced form is metabolized to phosphate by the plant and/or the fungus to support growth and productivity of the plant.

H. A method of fertilizing the plant of paragraph C, the method comprising: applying at least one reduced form of phosphorus to the plant and/or to soil adjacent the plant, such that the reduced form is metabolized to phosphate by the plant to support growth and productivity of the plant. Optionally, the reduced form may be applied as foliar fertilizer or added to amend soil to provide a source of phosphate to sustain plant growth and reproduction of the plant.

I. A method of treating water to lower its content of reduced phosphorus, the method comprising: contacting water containing hypophosphite and/or phosphite with a plurality of the plant cells and/or fungal cells comprising the nucleic acid of paragraph A, such that at least a portion of the hypophosphite and/or phosphite is oxidized to phosphite and/or phosphate. Optionally, the step of contacting includes a step of contacting the water with a plurality of vascular plants composed of plant cells comprising the nucleic acid of paragraph A.

J. A method of treating liquid waste to lower its content of reduced phosphorus, the method comprising: contacting (i) water containing hypophosphite and/or phosphite as a contaminant and (ii) a plurality of the plant cells and/or fungal cells comprising the nucleic of paragraph A, such that at least a portion of the hypophosphite and/or phosphite is oxidized to phosphite and/or phosphate.

K. A method of utilizing the nucleic acid of paragraph A for production of a transgenic plant, comprising: selecting for growth of plant cells comprising the nucleic acid of paragraph A as a selectable marker during production of a transgenic plant.

L. A method of obtaining a plant transformed with a nucleic acid encoding a phosphite dehydrogenase enzyme that is expressible from the nucleic acid as a selectable marker, comprising: contacting plant cells and a composition including the nucleic acid under conditions that promote introduction of the nucleic acid into at least a subset of the plant cells; culturing the plant cells in a medium containing phosphite as a primary or exclusive phosphorus source for growth; selecting transformed plant cells produced by the steps of contacting and culturing, and expressing the phosphite dehydrogenase enzyme as evidenced by growth in the medium; and regenerating at least a portion of the transformed plant cells into a transgenic plant. The method of this paragraph may be described further as follows: (L1) wherein the composition includes *Agrobacterium* cells that supply the nucleic acid during the step of contacting; or (L2) wherein the composition includes projectiles that are fired at the plant cells in the step of contacting.

M. A plant, comprising: a nucleic acid including a chimeric gene expressing a phosphite dehydrogenase enzyme such that the plant is capable of metabolizing phosphite (Phi) as a phosphorus source for supporting growth, thereby enabling growth of the plant without an external source of phosphate (Pi). The plant of this paragraph may be described further as follows: (M1) wherein the nucleic acid is stably integrated into the genome of the plant; (M2) wherein the plant is a vascular plant; (M3) wherein the plant is a species of algae; (M4) wherein the phosphite dehydrogenase enzyme has any of the features of paragraph A; or (M5) any combination of M1 through M4.

N. A fungus, comprising: a nucleic acid including a chimeric gene expressing a phosphite dehydrogenase enzyme such that the fungus is capable of metabolizing phosphite (Phi) as a phosphorus source for supporting growth, thereby enabling growth of the fungus without an external source of phosphate (Pi). The fungus of this paragraph may be described further as follows: (N1) wherein the nucleic acid is stably integrated into the genome of the fungus; (N2) wherein the fungus is a species of *Trichoderma*; (N3) wherein the fungus is a mycorrhizal species capable of forming a symbiotic relationship with a plant; (N4) further comprising a plant associated with the fungus to form mycorrhizae; (N5) wherein the phosphite dehydrogenase enzyme has any of the features of paragraph A; or (N6) any combination of N1 through N5.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

---

We claim:

1. A method of fertilizing a crop plant using phosphite as a phosphorus source for supporting growth, the crop plant including a plurality of cells comprising a nucleic acid comprising a chimeric gene including (a) a coding region that encodes an enzyme that catalyzes oxidation of phosphite to phosphate, wherein the enzyme is a phosphite dehydrogenase enzyme and (b) a transcription promoter operatively linked to the coding region, wherein the promoter is heterologous with respect to the coding region and is functional in plants, and wherein the chimeric gene provides sufficient expression of the enzyme in a plant containing the chimeric gene to confer an ability on the plant to metabolize phosphite as a phosphorus source for supporting growth, thereby enabling growth of the plant without an external source of phosphate, the method comprising:
   applying phosphite to the plant and/or to soil adjacent the plant, such that the phosphite is metabolized to phosphate by the plant to support growth and productivity of the plant.

2. The method of claim 1, wherein the enzyme is expressed from a nucleic acid construct including a plant promoter operatively linked to a coding sequence for the enzyme.

3. The method of claim 2, wherein the nucleic acid construct comprises a plant promoter that is induced by low phosphate conditions.

4. The method of claim 1, wherein the enzyme is expressed from a nucleic acid construct including a viral promoter operatively linked to a coding sequence for the enzyme.

5. The method of claim 4, wherein the viral promoter corresponds to the 35S promoter of Cauliflower Mosaic Virus.

6. The method of claim 1, wherein the crop plant is grown in the presence of sufficient phosphite to selectively promote growth of the plant relative to weeds near the plant.

7. The method of claim 1, wherein the phosphite is applied as a foliar fertilizer.

8. The method of claim 1, wherein the phosphite is applied as a soil amendment.

9. The method of claim 1, wherein the species of crop plant is selected from the group consisting of maize, soybean, rice, potatoes, tomatoes, sugarcane, and wheat.

10. The method of claim 1, wherein the crop plant produces a commercial oil.

11. The method of claim 1, wherein the enzyme is of bacterial origin.

12. The method of claim 1, wherein the phosphite dehydrogenase enzyme is PtxD of *Pseudomonas stutzeri*.

13. The method of claim 1, wherein the enzyme has an amino acid sequence including a first sequence region having an NAD-binding motif with sequence VGILGMGAIG (SEQ ID NO:15), a second sequence region having sequence XPGALLVNPCRGSVVD (SEQ ID NO:16), where X is K or R, and a third sequence region having sequence $GWX_1PX_2X_3YX_4X_5GL$ (SEQ ID NO:19), where $X_1$ is R, Q, T, or K, $X_2$ is A, V, Q, R, K, H, or E, $X_3$ is L or F, $X_4$ is G, F, or S, and $X_5$ is T, R, M, L, A, or S.

14. The method of claim 1, wherein the crop plant forms mycorrhizae with a mycorrhizal fungus transgenically modified to express a phosphite dehydrogenase enzyme capable of catalyzing oxidation of phosphite to phosphate.

15. The method of claim 1, wherein the crop plant is associated with a *Trichoderma* fungus transgenically modified to express a phosphite dehydrogenase enzyme capable of catalyzing oxidation of phosphite to phosphate.

* * * * *